US010955995B2

(12) United States Patent
Burch et al.

(10) Patent No.: US 10,955,995 B2
(45) Date of Patent: Mar. 23, 2021

(54) SYSTEM AND METHOD FOR USER INTERFACE MANAGEMENT FOR MEDICAL CARE MANAGEMENT DEVICES

(71) Applicant: Christiana Care Health System, Inc., Wilmington, DE (US)

(72) Inventors: Catherine Burch, Bear, DE (US); Erwin V. Bautista, Aston, PA (US); Michael G. Benninghoff, Coatesville, PA (US); John Gerard DiGiovanni, Wilmington, DE (US); Mithil Gajera, Marlton, NJ (US); Jason A. Mastriana, Newark, DE (US); Jonathan Michael Meade, Newark, NJ (US); Dannette Arlene Newby Mitchell, New Castle, DE (US); Bridget A. Remel, Cochranville, PA (US); Nelida Rios, Newark, DE (US); Wen Shen, Newark, DE (US)

(73) Assignee: CHRISTIANA CARE HEALTH SYSTEM, INC., Wilmington, DE (US)

( * ) Notice: Subject to any disclaimer, the term of this patent is extended or adjusted under 35 U.S.C. 154(b) by 0 days.

(21) Appl. No.: 16/106,198

(22) Filed: Aug. 21, 2018

(65) Prior Publication Data
US 2019/0079642 A1    Mar. 14, 2019

Related U.S. Application Data

(60) Provisional application No. 62/555,929, filed on Sep. 8, 2017.

(51) Int. Cl.
*G06F 3/0482* (2013.01)
*G16H 50/20* (2018.01)
(Continued)

(52) U.S. Cl.
CPC .......... *G06F 3/0482* (2013.01); *G16H 40/20* (2018.01); *G16H 40/67* (2018.01); *G16H 50/20* (2018.01)

(58) Field of Classification Search
CPC ....... G06F 3/0482; G16H 50/20; G16H 40/67
See application file for complete search history.

(56) References Cited

U.S. PATENT DOCUMENTS

| 2005/0135195 | A1* | 6/2005 | Kreidler | G04F 1/005 368/107 |
| 2006/0136998 | A1* | 6/2006 | Oowaki | G06F 21/31 726/5 |

(Continued)

OTHER PUBLICATIONS

ACLS Advisor application for smart phones, by Paul Chan, released Sep. 3, 2015, downloaded Oct. 21, 2016; information sheet enclosed.
(Continued)

*Primary Examiner* — Seth A Silverman
(74) *Attorney, Agent, or Firm* — Fisherbroyles, LLP

(57) ABSTRACT

A system and method for controlling a computerized device's display to provide a user interface that renders compact and informative graphical user interface images, particularly in a medical care management device in which a large amount of information is required by the user, and a size of the display device is relatively small. The system and method can deliver structured guidance to medical personnel to promote rendering of medical care in compliance with predetermined care protocols, and automatedly logs, and/or guides the user to log, events and occurrences during the medical emergency for accurate logging of same. Multiple independent cyclical numerical task timers, graphical progress indicators, and cycle counters may be displayed concurrently within a single field of view/window within a display device's display area. Expiration of a cycle time may (Continued)

be reflected by a color change, and initiate text or other prompting according to a predefined care protocol.

50 Claims, 45 Drawing Sheets

(51) Int. Cl.
*G16H 40/67* (2018.01)
*G16H 40/20* (2018.01)

(56) References Cited

U.S. PATENT DOCUMENTS

| | | | | |
|---|---|---|---|---|
| 2009/0168975 | A1* | 7/2009 | Clawson | G16H 10/20 379/45 |
| 2014/0310041 | A1* | 10/2014 | Crocker | G06Q 10/06311 705/7.15 |
| 2015/0205511 | A1* | 7/2015 | Vinna | G06F 3/0481 715/716 |
| 2017/0020461 | A1* | 1/2017 | Quinn | A61B 5/7275 |
| 2017/0102846 | A1* | 4/2017 | Ebler | A61M 1/3626 |

OTHER PUBLICATIONS

ACLS Fast application for smart phones, created by Crystal Clear Solutions, released Jul. 22, 2013, downloaded May 29, 2018; information sheet enclosed.

CARMA for life application for smart phones, created by ACLS Solutions, LLC, released Mar. 6, 2015, downloaded Oct. 21, 2016; information sheet enclosed.

Code Blue Assist application for smart phones, created by Lauren Smith, published 2017, downloaded May 29, 2018; information sheet enclosed.

Code Blue: CPR Event Timer application for smart phones, created by Erik Santana, released Jul. 2, 2015, downloaded Oct. 21, 2016; information sheet enclosed.

Code CPR 5 application for smart phones, created by Remarkable Edge, Lda, released Apr. 24, 2013, downloaded May 29, 2018; information sheet enclosed.

Code Runner Pro application for smart phones, created by Angel Vazquez, released Dec. 19, 2017, downloaded May 29, 2018; information sheet enclosed.

CPR Tempo application for smart phones, created by Frozen Ape Pte. Ltd., released Sep. 18, 2012, downlaoded May 29, 2018; information sheet enclosed.

CPR Timer application for smart phones, created by Samuel Maljaars, released Apr. 20, 2016, downloaded May 29, 2018; information sheet enclosed.

EventDoc application for tablets, created by Format Health, information retrieved from https://formathealth.com/how-it-works/, date unknown; information sheet enclosed.

Full Code Pro application for smart phones, created by the American Heart Association, released Jan. 16, 2013, downloaded May 29, 2018; information sheet enclosed.

MediCode application for smart phones, created by the National Health Care Provider Solutions, released May 26, 2013, downloaded May 29, 2018; information sheet enclosed.

\* cited by examiner

Sign-Off

Sign-Off Notes

Outcome

Patient Status — Alive

Pre-Arrival

| | |
|---|---|
| Code Date | 12/16/2016 |
| Code Time | 13:31:12 |
| Location | Christiana - 2A SCCC |
| CPR Started Before Code Team Arrived | Yes |
| Breathing Prior to Onset | Endotracheal Tube (ETT) |
| Monitors Present Prior to Onset | Electrocardiogram (ECG) |
| IV Access Prior to Onset | Femoral |
| AED Applied | Yes |
| AED Shock | Yes |

Activity Log — View Activity Log

- Stop Recording
- Start CPR
- Pulse Check
- Stop CPR
- Respiration Check
- Epinephrine - 1 mg
- Start CPR
- Stop CPR
- Rhythm Check
- Intubation
- Shock - 150 Joules
- Start CPR

Fig. 41

Pre-Arrival

| | |
|---|---|
| Code Date | 12/18/2018 |
| Code Time | 13:31:12 |
| Location | Christiana - 2A SCCC |
| CPR Started Before Code Team Arrived | Yes |
| Breathing Prior to Onset | Endotracheal Tube (ETT) |
| Monitors Present Prior to Onset | Electrocardiogram (ECG) |
| IV Access Prior to Onset | Femoral |
| AED Applied | Yes |
| AED Shock | Yes |

Patient Demographics

| | |
|---|---|
| Patient FIN | Required Field |
| Patient Name (Last, Name) | Required Field |
| Patient Date of Birth (MM/DD/YYYY) | Required Field |

Clinical Sign-off

| | |
|---|---|
| Code Chief/Clinical Leader Name | Required Field |
| Code Chief/Clinical Leader Badge ID | Required Field |

Activity Log

- Stop Recording
- Start CPR
- Pulse Check
- Stop CPR
- Respiration Check
- Epinephrine - 1 mg
- Start CPR
- Stop CPR
- Rhythm Check
- Intubation
- Shock - 150 Joules
- Start CPR

Activity Log

| Time | Action | Details | |
|---|---|---|---|
| 13:36:01 | Stop Recording | Reason Ended ROSC; Atrial Fibrillation (AF); Blood Pressure at ROSC 85 | Select the Rhythm at ROSC; What is End Tidal at ROSC N/A | Edit |
| 13:37:29 | Start CPR | | Edit |
| 13:37:29 | Pulse Check | Is there a pulse? No; Total 31:30 | Rhythm PEA; What is End | Edit |
| 13:37:29 | Stop CPR | | Edit |
| 13:36:47 | Respiration Check | | Edit |
| 13:35:41 | Epinephrine - 1 mg | | Edit |
| 13:36:32 | Start CPR | | Edit |
| 13:35:31 | Pulse Check | Is there a pulse? No; Total PEA | Rhythm Asystole; What is End | Edit |
| 13:35:27 | Stop CPR | | Edit |

Fig. 45

SYSTEM AND METHOD FOR USER INTERFACE MANAGEMENT FOR MEDICAL CARE MANAGEMENT DEVICES

CROSS-REFERENCE TO RELATED APPLICATION

This application claims the benefit of U.S. Provisional Patent Application No. 62/555,929, filed Sep. 8, 2017, the entire disclosure of which is hereby incorporated herein by reference.

FIELD OF THE INVENTION

The present invention relates generally to the field of computer information systems and medical decision support systems, and more particularly, to a computerized system and method providing a user interface for medical care management devices that delivers structured guidance to medical personnel during a medical emergency according to a predetermined protocol, and automated logging of events and occurrences during the medical emergency. As such, the system acts as a tool for one or more healthcare professionals seeking to administer medical care in an emergency, the system's user interface presenting a dense combination of information in support of proper medical care to ensure compliance with a predetermined care protocol and/or to accurately record events and occurrences in support of proper medical and administrative procedures.

BACKGROUND

There are various contexts in which a graphical user interface display needs to be controlled and managed. One such context involves medical care management devices. There are challenges in rendering accurate and adequately informative graphical user interface images for a user, particularly when a large amount of information is required by the user, and when a size of the display device is relatively small, as is the case with common smartphone and tablet computing devices.

Further, in many contexts, there is a need for healthcare professionals to follow predetermined care protocols, and to keep accurate medical records. These needs can be particularly acute in the case of medical emergencies. In such emergencies, it can be particularly important to follow predetermined care protocols, as failure to do so could result in severe injury or death to a patient. Further, it is important for the peace of mind of the patient's loved ones, and to mitigate and/or prevent liability for the healthcare professional and/or related health care institution, to be able to document that the predetermined care protocols were followed. Unfortunately, the emergency medical care environment can be chaotic, and the patient's needs may be acute and immediate, and thus it may be particularly difficult for healthcare professionals to ensure compliance with predetermined care protocols, and to fully document such compliance, during such medical emergencies.

By way of example, so-called "code" medical emergencies, such as a Code Blue, may require a team of healthcare professionals to rush to administer aid to a patient in need. Such medical emergencies may occur, for example, in a healthcare system, medical aid unit, hospital, nursing home and/or assisted living facility environments. By way of further example, a "Code Blue" is a cardiopulmonary arrest emergency that requires healthcare professionals to administer drugs and perform CPR to restore cardiac perfusion and oxygen delivery as soon as possible. This is the primary goal of cardiac arrest resuscitation care. Evidence based, universally accepted "best practice" or "standard of care" protocols exist that are written from consensus expert opinion to ensure that the Code Blue response team follows the best Advanced Cardia Life Support (ACLS) protocols to give the patient the best odds to survive the event. By way of non-limiting example, the American Heart Association provides guidelines in the form of a predetermined care protocol that should be followed by healthcare providers when providing care in a Code Blue event. The protocol generally provides defined tasks, task sequences, etc. and intervals for performing such events. The tasks are intended to promote the best next action with the goal of survival.

In a typical scenario, one or more persons may be responsible for recording the occurrence of events, timing of events, etc., and one or more persons may be responsible for administering care according to the protocol, and reporting those events for manual documentation, e.g., using a stopwatch and clipboard, in paper form. Due to the complexities of the situation and the chaotic nature of a medical emergency, it is common for a predetermined care protocol to be followed with less-than-ideal accuracy, because of gaps or deficiencies in the training of the medical personnel, errors in recall or application of proper procedures, and/or ineffective collaboration and/or inaccurate synchronization among the various members of the medical care team and various clocks/timers.

It is likely even more common for record keeping with respect to the following of the care protocol to include errors and/or be incomplete. In the medical field, there are estimates that approximately 30%-40% of Code Blue documentation is missing, incomplete or incorrect, due the chaotic nature of Code Blue events, and the higher priority given to providing life-saving care to the patient than to the secondary task of recording the details of the aspects of the care provided.

Smartphone and tablet computing devices exist, but have display screen areas that are relatively limited in physical size, and that are especially limited in view of the amount of information required to be managed in a medical care or medical emergency context, particularly in the Code Blue context for which tasks are typically allocated to multiple personnel due to the large amount of information that must be managed in reliably accurate fashion. Such devices do not provide adequate displays of information, and in particular, adequate displays of information that are sufficiently compact to be displayed within a single viewing area of a physical display region of such devices, so that the need for scrolling or navigating among multiple windows, is avoided, and so that all relevant information is displayed within a single field of view.

What is needed is a system and method for controlling a display of a computerized device to provide a graphical user interface that renders adequately informative graphical user interface images for a user, particularly in a medical care management device in which a large amount of information is required by the user, and a size of the display device is relatively small, as is the case with common smartphone and tablet computing devices.

SUMMARY

The present invention provides a computerized system and method for controlling a display of a computerized device to provide a graphical user interface that renders compact and informative graphical user interface images, particularly in a medical care management device in which a large amount of information is required by the user, and a size of the display device is relatively small, as is the case with common smartphone and tablet computing devices. The system and method can deliver structured guidance to medical personnel, e.g., during a medical emergency, to promote rendering of medical care in compliance with predetermined care protocols, and automatedly logs, and/or guides the user to log, events and occurrences during the medical emergency for accurate logging of same.

In one embodiment, an exemplary computerized care support system comprises: a display device; a user input component; a memory operatively comprising a non-transitory data processor-readable medium; a data processor operatively connected to the memory, the display and the user input component; and user interface management instructions embodied in data processor-executable code stored in the memory, said user interface management instructions being executable by the data processor to provide a user interface display engine configured to: display, via the display device, an entire management interface window within a physical display area of the display device; display within the window, via the display device, a free-running session timer; display within the window, via the display device, a plurality of independent cyclical task timers, each of said plurality of independent cyclical task timers having a different respective time interval cycle and corresponding to a distinct task; and in response to expiration of any one of said plurality of independent cyclical task timers: display within the window, via the display device, at least one prompt corresponding to the expiration of said any one of said plurality of independent cyclical task times, said prompt being specified a predetermined care protocol.

Alternative system embodiments, methods and computer program products are provided also.

BRIEF DESCRIPTION OF THE FIGURES

An understanding of the following description will be facilitated by reference to the attached drawings, in which:

FIGS. 4-45 show exemplary user interface windows of the emergency management interface in accordance with the present invention.

DETAILED DESCRIPTION

The present invention provides a computerized system and method for controlling a display of a computerized device to provide a graphical user interface that renders compact and informative graphical user interface images, particularly in a medical care management device in which a large amount of information is required by the user, and a size of the display device is relatively small, as is the case with common smartphone and tablet computing devices. The system and method delivers structured guidance to medical personnel during a medical emergency to promote rendering of medical care in compliance with predetermined care protocols, and that automatedly logs, and/or guides the user to log, events and occurrences during the medical emergency for accurate logging of same.

Figure 1:
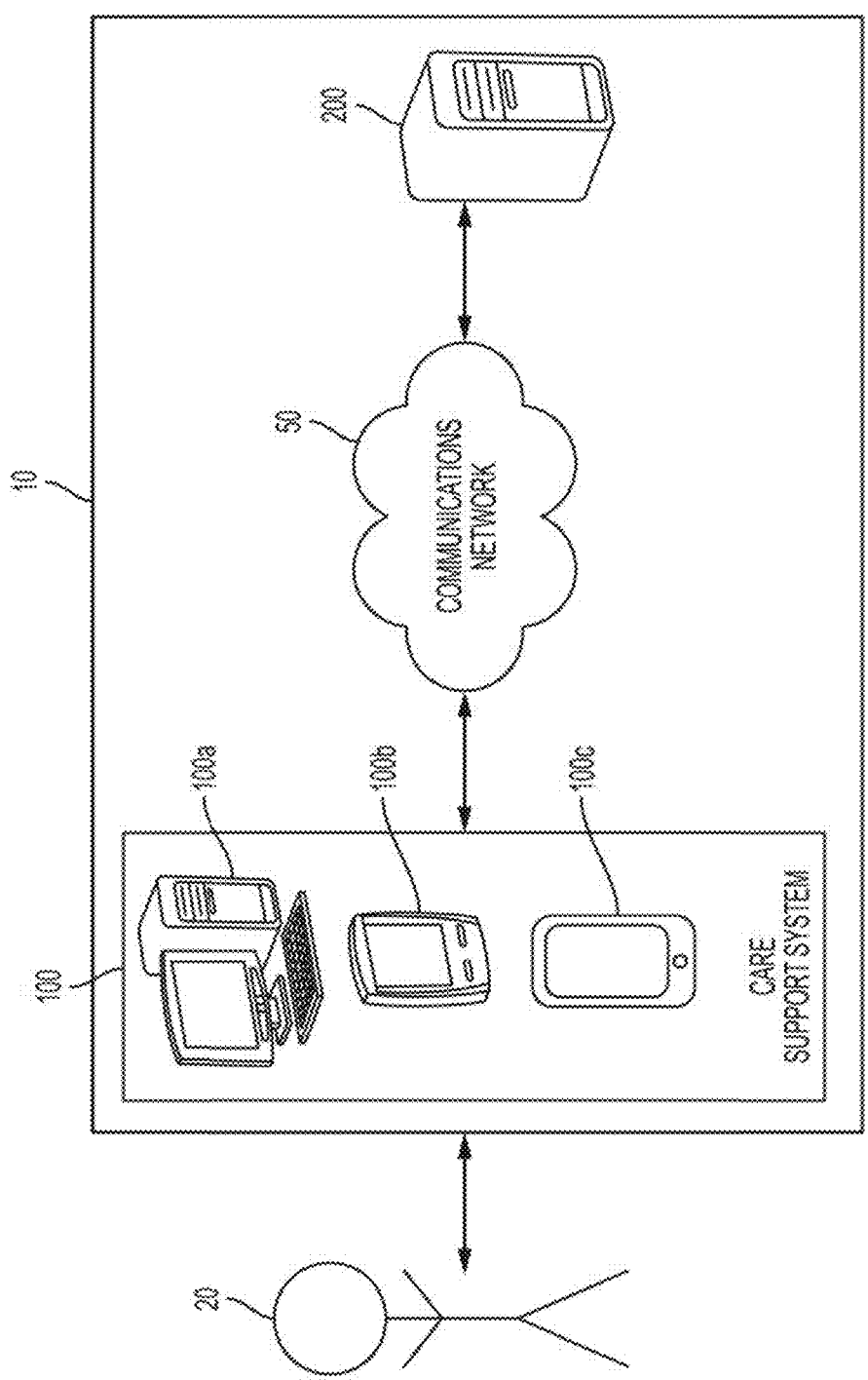
FIG. 1 is a diagrammatic view of an exemplary networked computing environment implementing systems and methods for promoting rendering of medical care in compliance with predetermined care protocols and for accurate logging of same in accordance with the present invention.

Referring now to FIG. 1, a diagrammatic view of an exemplary networked computing environment 10 is shown for implementing systems and methods in accordance with the present invention. As shown in the example of FIG. 1, a user (such as a healthcare professional) 20 interacts with an emergency management interface environment provided via an Care Support System (CSS) 100 in accordance with the present invention. The CSS 100 may comprise a personal computing-type device, which may be a desktop, laptop, or notebook computer 100a, a smartphone 100b, or a tablet PC 100c, such as an iPad manufactured and/or distributed by Apple, Inc. or a Google Android-based device, that stores and executes special-purpose software providing the special-purpose CSS described herein. The CSS 100 may receive and store software executable to provide the virtual world-based system described herein in standalone fashion. Alternatively, the CSS may act as a client device communicating over a communications network 50 with a system 200 acting as a server to cause display of a graphical user interface at the client device that provides the emergency management interface with which the user may interact. In either case, data may be communicated from the CSS 100 over the network to a system 200 for further processing, analysis and/or storage, as described herein.

The components of the networked environment 10 can be interconnected in any suitable configuration, using any suitable type of connection and conventional communications hardware and software. The components may be connected directly or over a network 50, which may be any suitable network. For example, one or more portions of network 50 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, another type of network, or a combination of two or more such networks.

The components of the networked environment 10 may be connected to each other using any suitable communication connections. For example, suitable connections include wireline (e.g., DSL or DOCSIS), wireless (e.g., WiMAX), and optical (e.g., SONET SDH) connections. For example, one or more connections may include an intranet, extranet, VPN, LAN, WAN, cellular telephone network or other type of connection or combination of connections.

Figure 2:
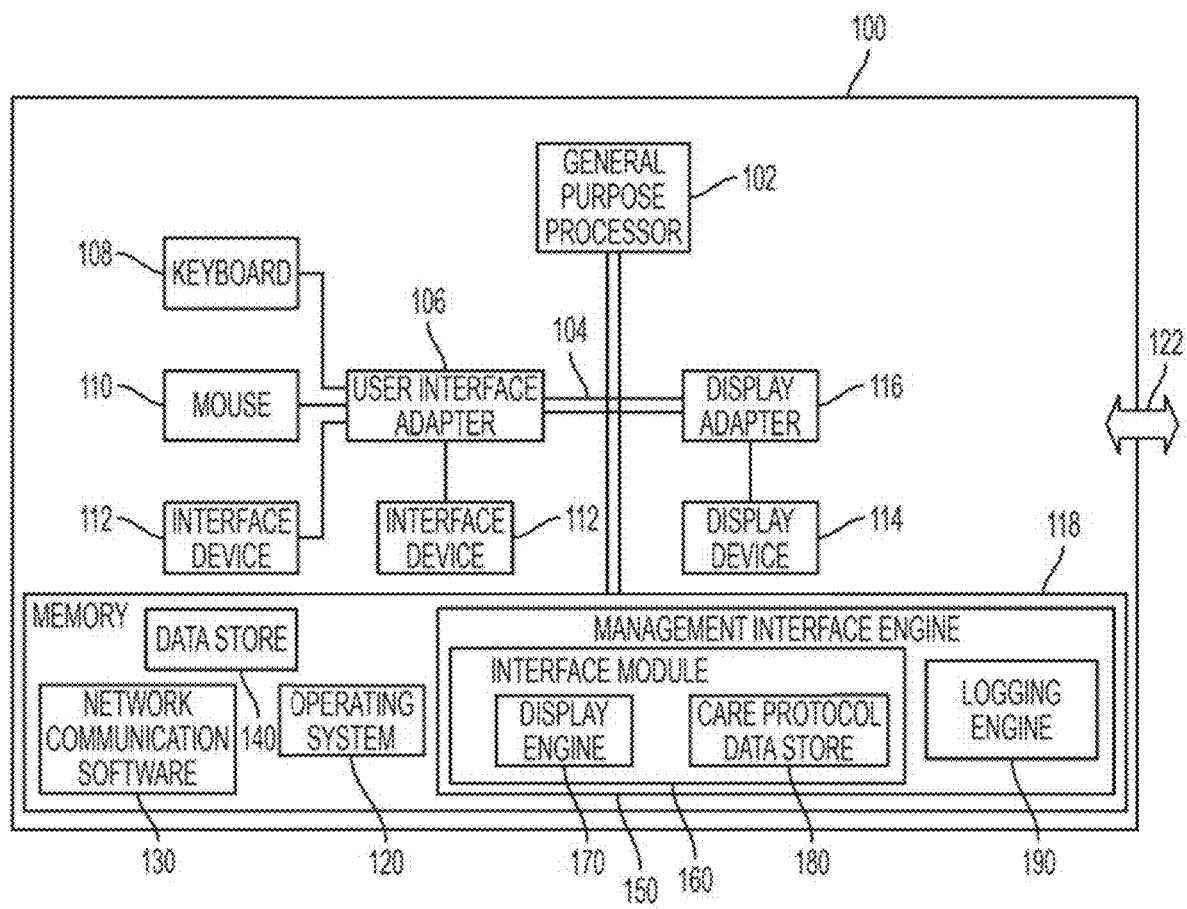
FIG. 2 is a diagrammatic view of an exemplary Care Support System in accordance with the present invention.

As will be appreciated from FIG. 2, the CSS 100 may include generally conventional computing hardware and software for general operation. FIG. 2 is a block diagram showing an exemplary CSS 100 in accordance with an exemplary embodiment of the present invention. However, the CSS 100 is a special-purpose computerized system that includes conventional hardware, e.g. one or more processors, memory hardware storing and executing both conventional software enabling operation of a general purpose computing system, such as operating system software 120 and network communication software 130, and specially-configured computer software for configuring the general purpose hardware as a special-purpose computing system for carrying out at least one method in accordance with the present invention.

Accordingly, the computing device 100 of FIG. 2 includes a general-purpose processor, such as a microprocessor (CPU) 102 and a bus 104 employed to connect and enable communication between the processor 102 and the components of the presentation system in accordance with known techniques. The exemplary CSS 100 includes a user interface adapter 106, which connects the processor 102 via the bus 104 to one or more interface devices, such as a keyboard 108, mouse 110, and/or other user input components 112, which can be any user interface device, such as a touch-sensitive screen, digitized entry pad, etc. The bus 104 also connects a display device 114, such as an LCD screen or monitor, to the processor 102 via a display adapter 116. The bus 104 also connects the processor 102 to memory 118, which can include solid state memory, a hard drive, diskette drive, tape drive, etc.

The CSS 100 may communicate with other computers or networks of computers, for example via a communications channel, network card or modem 122. The CSS 100 may be associated with such other computers in a local area network (LAN) or a wide area network (WAN), and may operate as a client in a client/server arrangement with another computer, etc. Such configurations, as well as the appropriate communications hardware and software, are known in the art.

The CSS 100 is specially-configured in accordance with the present invention in that it includes various engines and modules, each of which is effectively a combination of computing hardware and computer-readable, processor-executable instructions stored in memory of computing hardware. The CSS 100 includes an Interface Engine (IE) 150, which comprises computer-readable, processor-executable instructions stored in the memory for carrying out the methods described herein. Further, the memory stores certain data, e.g. in a database or other data store 140 shown logically in FIG. 2 for illustrative purposes, without regard to any particular embodiment in one or more hardware or software components. Optionally, other software and/or data may be stored in a corresponding data store 140 of the memory 118. The IE 150 receives and processes data, and causes display of the management user interface in accordance with the teachings of the present invention. Accordingly, the IE 150 includes rules and logic implementing the analysis and method steps described herein.

Notably, the IE 150 includes an Interface Module (IM) 160. The IM 160 is configured to control the management interface, and to provide and receive data via the interface, in accordance with the present invention. The IM 160 includes data, rules and instructions for displaying the images of the graphical user interface, including the various elements of the graphical user interface images. In accordance with the present invention, the IM includes a Display Engine (DE) 170 that is configured to display the graphical user interface images, to provide information and receive user input. Accordingly, the DE 170 includes data, rules and instructions for displaying multiple numerical timers concurrently, for displaying a timer that counts upward to reflect elapsed time, and that continues running even after a predetermined interval has expired, for displaying a visual progress bar providing a graphical representation of both elapsed interval time and remaining interval time, e.g., by color and/or shading, for display of a cumulative count in numeric form that indicates a number of partial or completed cycles/time intervals for each timer, for displaying an interval expiration indication, such as a color change of the timer and/or progress bar, and for displaying guided prompts, in a time-based fashion upon expiration of timers and/or time intervals, and/or in a branched logic fashion based on user input gathered via the user interface, e.g., in the form of instructive text and menus of user-selectable inputs/responses. Further, in accordance with the present invention, the IM 160 includes a Care Protocol Data Store (CPDS) 180. The CPDS 180 stores care protocols, such as the American Heart Association protocol, and/or stores at least one set of instructions for use by the IM 160 to display an interface in accordance with the care protocol, e.g., for example, to display the guided prompts at various times, etc., and/or to display the instructive text and menus, etc. By way of example, a care protocol may specify for performance of chest compressions/CPR for a 2-minute interval, followed by checking pulse, followed by another 2-minute cycle of chest compressions/CPR, etc. In this manner, the IM 160 manages information input and information output via the CSS 100.

Further, the IE 150 includes a Logging Engine (LE) 190. The LE 190 includes data, rules and instructions to record and create an electronic record of the corresponding medical emergency, including details relating to patient information and observations, data gathered, care rendering, timing of associated events, etc. Notably, this record is crafted to confirm that care was rendered in accordance with the corresponding care protocol stored in the care protocol data store 180. In this manner, the LE 190 records and creates a record of associated care information, and so, for example, can provide documentation of the "code" event. For example, the record may identify start and stop times of CPR intervals, a time of occurrence of a pulse check, a time of epinephrine delivery (and dosage), time of a respiration check (and a result of the check), etc.

Further, the LE 190 includes data, rules and instructions for controlling the display engine to display a scrolling event log identifying event occurrences. Accordingly, the LE 190 may include instructions for recognizing input to the system, and for time-stamping such input, for storing associated data, and for interfacing with the DE to display such event occurrences in a defined portion of the display window, preferably within the same field of view of the timers, etc., which contributes to a particularly compact and information-dense rendering of information in the graphical user interface. The LE and/or the DE may provide for display of such results in a rolling or scrolling fashion so that the most recent results are always displayed, to the extent the size of the associated display region permits. Additionally, the LE 190 may include instructions for requiring, as desired, system log-in credentials, e.g., by way of typing alphanumeric strings, scanning a bar code or other identifying indicia on a personnel identification card, etc. The LE 190 may require entry of appropriate credentials and prevent access to a remainder of the functionality of the system until credentials have been provided, to promote compliance with desired record-keeping procedures.

Further still, the LE 190 may be configured to prevent a log-out to close a session, or to start a new session, until all desired input has been gathered, in accordance data in the CPDS or other data indicating associated requirements. In this manner, the LE 190 may prevent access to a remainder of the functionality of the system until desired input has been provided, to promote compliance with desired record-keeping procedures.

Still further, the LE 190 is configured to create and/or make accessible data files incorporating the logged data/information, so that data files of the recorded care sessions/events are available for subsequent data mining and/or data analysis. Accordingly, rather than merely provide static report output as a human-readable image file (such as a PDF or JPG formatted image file), the LE 190 may provide output in the form of a data file, such as a *.CSV file, an Excel file, or another data file including data in a readily processable fashion for use, processing and/or import by a data processing system.

In this exemplary embodiment, all of these components and the associated processing are provided/performed at the CSS 100. In certain embodiments, data gathered at the CSS 100 may be transmitted to a remote server, e.g., server 200, for subsequent storage, processing, correlation and/or analysis. In other embodiments, one or more of the functional components described above may be provided remotely, e.g., at server 200, rather than at the CSS 100, and such remotely located components may be accessed by the CSS 100 via communications network 50 during operation of the CSS 100.

Figure 3:
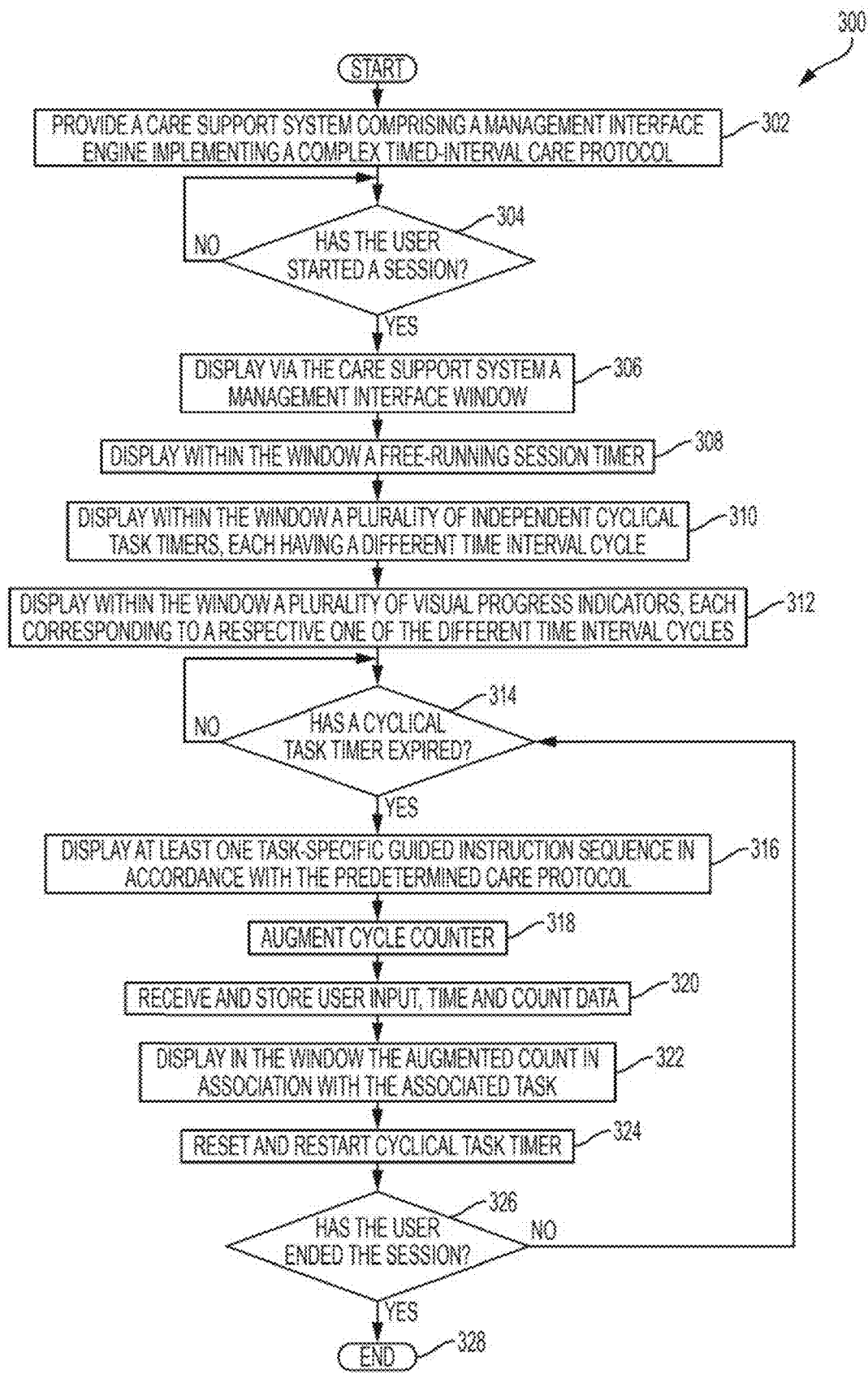
FIG. 3 is a flow diagram illustrating an exemplary method for promoting rendering of medical care in compliance with predetermined care protocols and for accurate logging of same.

Referring now to FIG. 3, a flow diagram 300 is provided that illustrates an exemplary method for controlling a user interface to promote rendering of medical care in compliance with predetermined care protocols and for accurate logging of same in accordance with the present invention. As shown in FIG. 3, this exemplary method begins with providing a Care Support System (CSS) 100 comprising an Interface Engine (IE) 150 in accordance with the present invention, as shown at 302. The IE may be implemented as software stored in the memory 118 of the CSS 100, and including computer-executable instructions for carrying out the method and/or providing the functionality described herein. By way of example, this may involve downloading a suitable software application to tablet computing hardware, e.g., from an "app store" or software application marketplace, and installing it to configure the general-purpose hardware as a special-purpose CSS in accordance with the present invention. Accordingly, the IE 150 includes the Interface Module (IM) 160, and thus the Display Engine (DE) 170 and Care Protocol Data Store 180, and the Logging Engine (LE) 190, as described above.

Referring again to FIG. 3, the method next involves determining if the user has started a session, as shown at 304. This may be performed by the DE 170 and/or IM 150, e.g., by continuously polling input components and/or monitoring for a predetermined input. By way of example, a user may start a session by tapping an icon displayed on a touchscreen of the tablet computing device to execute the software, and thereby "open" the corresponding "app." If this has not yet occurred, then the CSS waits in a continuing loop, as shown in FIG. 3.

Figure 4:
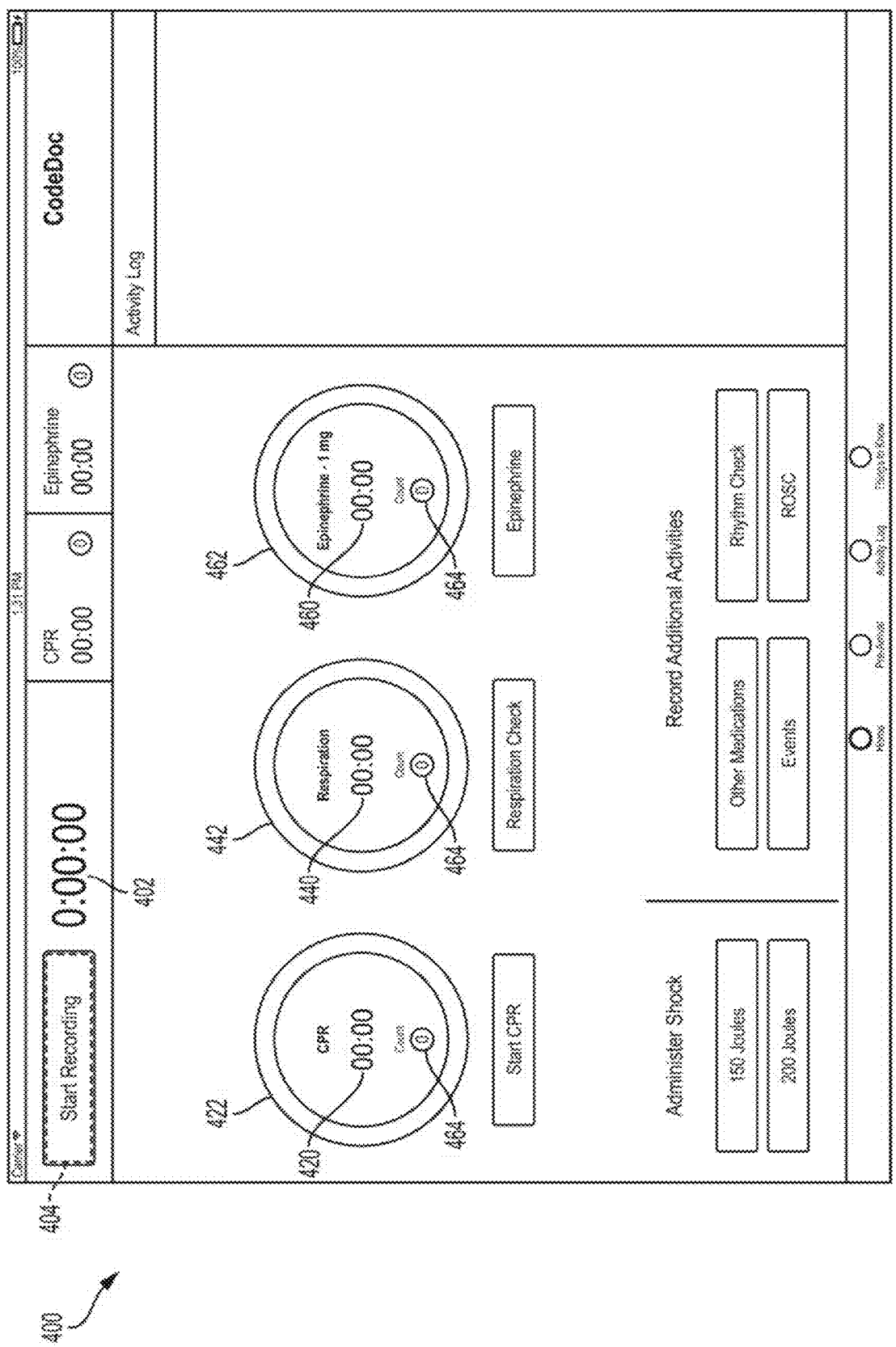

If it is determined at 304 that the user has started a session, then the method involves displaying via the CSS 100 a management interface window, as shown at 306. This may be performed by the DE 170 and/or IM 150. FIG. 4 shows an exemplary emergency management interface window 400. Preferably, the window is displayed such that the entire window is viewable concurrently on a corresponding display screen, within a physical display area of the physical display device, as shown in FIG. 4. This contributes to the compact and information-dense nature of the graphical user interface of the present invention.

In the exemplary method of FIG. 3, the method further involves displaying within the window 400 a free-running session timer, as shown at 308. Such a timer 402 is shown in FIG. 4. This timer counts and displays elapsed time for a session, particularly a "code" care session. This timer, and the associated session and associated functionality, may be started in response to actuation of an associated button 404 presented within the window 400. Once this timer has been started, the timer continues running to count upwardly, counting seconds, minutes and hours, until the user acts to end the session, end associated CSS functionality, and end associated logging of information. These tasks are controlled by the IE 150 and particularly the DE 170.

Referring again to FIG. 3, the method further involves displaying within the window 400 a plurality of independent cyclical task timers, each having a different time interval cycle, as shown at 310. In particular, the identity of these timers, and their cycle intervals, as displayed within the interface are governed by the care protocol implemented by the IE 150, as may be stored in the Care Protocol Data Store 180. Notably, the IE 150 may be configured to implement one or more care protocols stored in the Care Protocol Data Store 180, such that each cyclical task timer corresponds to a prescribed interval for a corresponding medical care task of the care protocol. This may be performed by the DE 170 with reference to CPDS 180.

In exemplary embodiment shown in FIGS. 4-45, the exemplary IE 150 implements the American Heart Association "Code Blue" care protocol, or a variation thereof. By way of example, an exemplary modified protocol calls for delivery of cardio-pulmonary resuscitation (CPR) care for 2 minutes followed by a pulse check, doing a respiration check every 3 minutes, and delivering epinephrine every 4 minutes. Accordingly, each of these timers has a different time interval cycle for each of these tasks. Accordingly, the exemplary window 400 displays a CPR timer 420, a Respiration Check Timer 440 and an Epinephrine Delivery timer 460.

Notably, IM 150 causes display of multiple such cyclical timers concurrently within a window within a single field of view on the display screen, so they can be viewed by a user simultaneously, to avoid the need to switch between graphical user interface windows. This contributes to display of information in a particularly compact form.

Further, each of these timers displays elapsed time in numerical form, in this case in minutes and seconds, counting upwardly. Further still, the DE 170 is configured to allow these timers to keep running even after expiration of a predetermined cycle time, rather than simply automatically restart the timer, so that the timer then shows an amount of time in excess of the predetermined cycle time, which communicates valuable information to the operator of the device in a particularly compact and information-dense form. Further, the DE 170 is configured to display the timer in a different color, or with a change in color of highlighting or another portion of the screen, upon expiration of the timer, even though the timer is permitted to keep running even after expiration of the predetermined cycle time. Using a color change to show expiration of the timer contributes to a compact display of information, as in fact it does not require any additional space within the graphical user interface window, and yet communicates additional information to the viewer.

Figure 5:
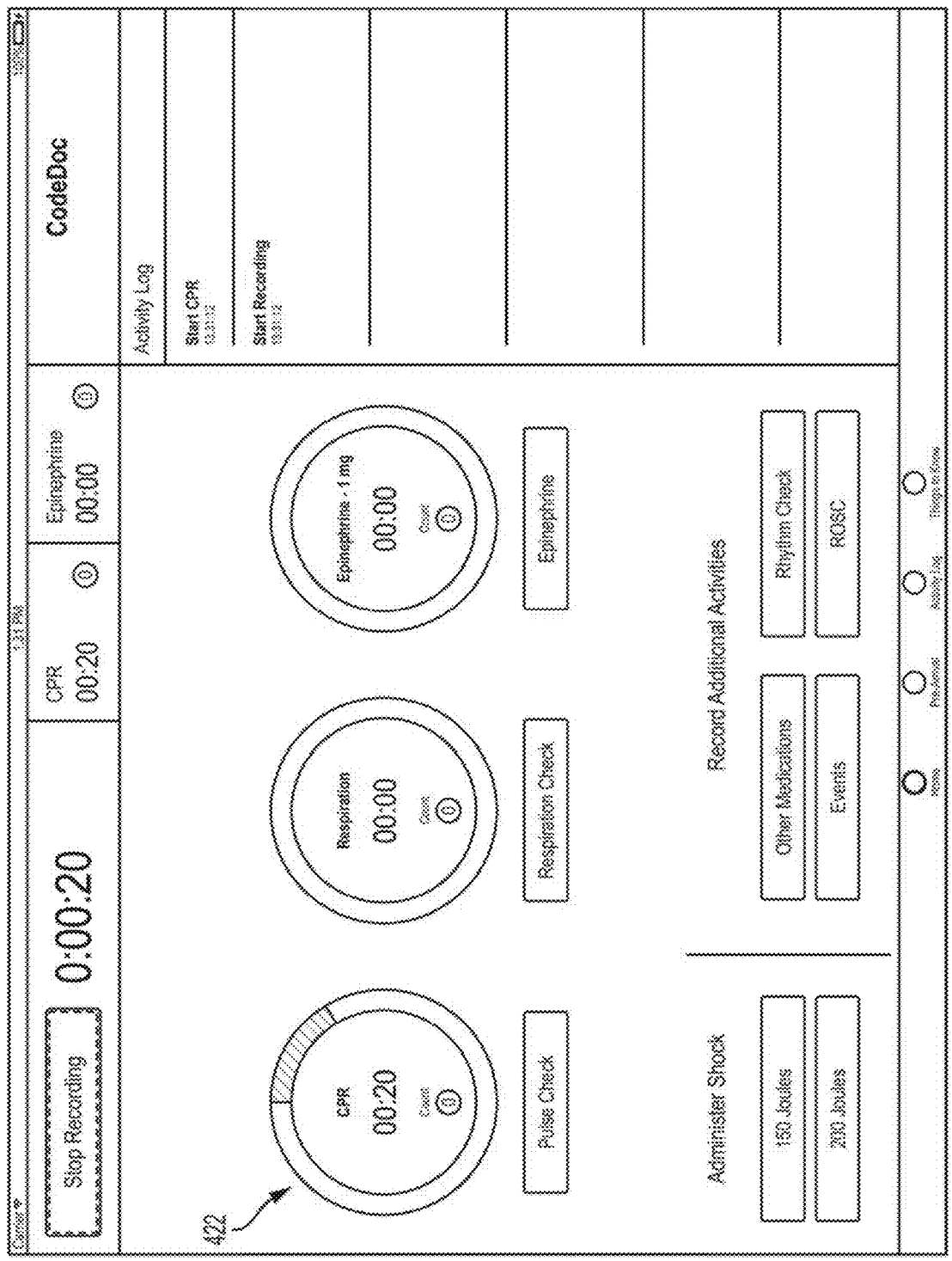
Figure 6:
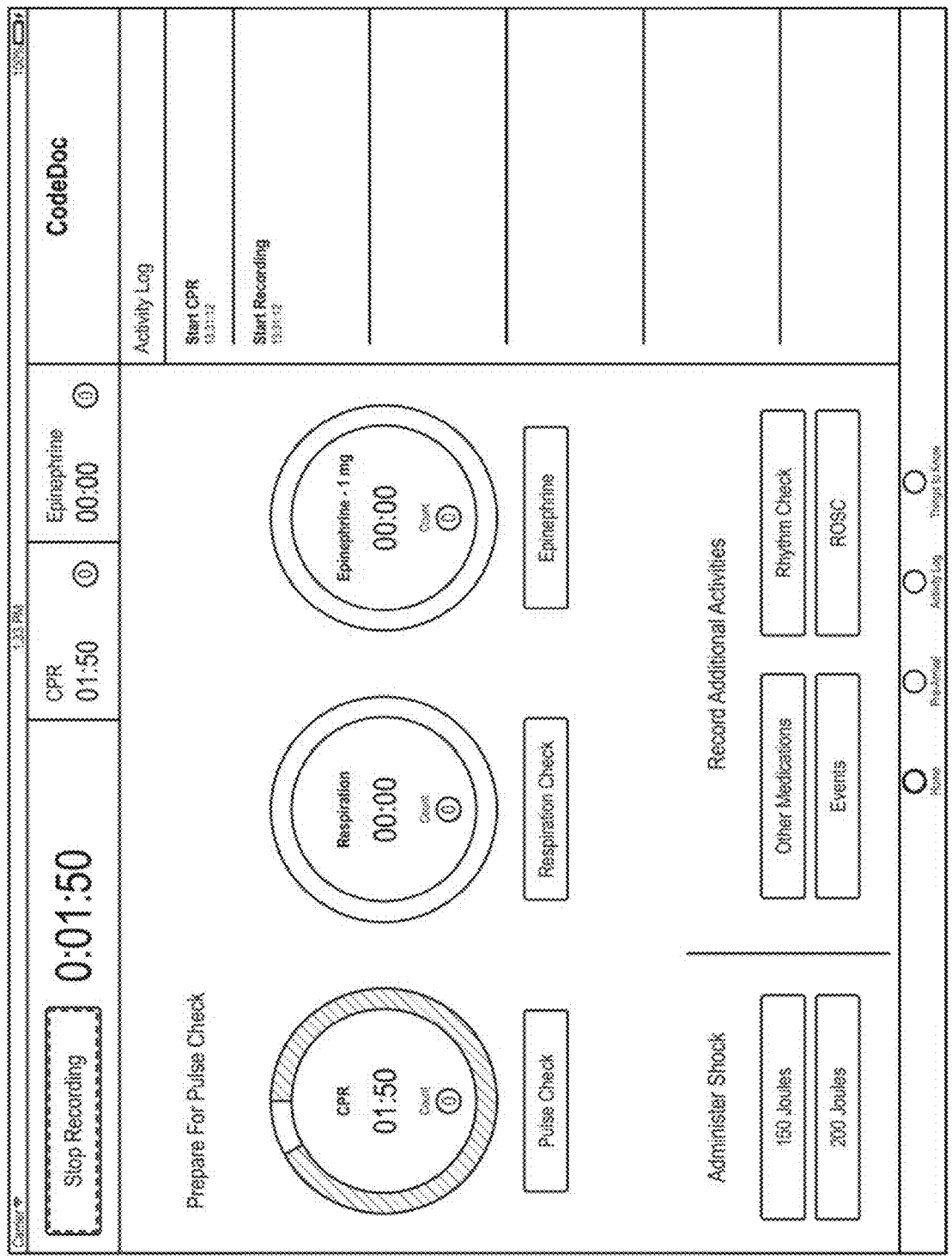

Further, the method involves display within the window 400 of a plurality of visual progress indicators. This is performed by the DE 170 in accordance with intervals defined in the CPDS 180. Each visual progress indicator corresponds to a respective one of the different time intervals, and to a respective one of the different timers. Accordingly, in the exemplary embodiment shown in FIG. 4, three visual progress indicators 422, 442, 462 are displayed. These visual progress indicators may have any form, but are characterized in that they show in visual form a degree of completion of elapsed time in a respective time cycle in non-numerical form, e.g., using shading and/or color. In FIG. 4, each visual progress indicator shows no progress (no elapsed time) in any of the individual timers. By way of example, FIG. 5 shows 20 seconds of progress, in visual, non-numeric form, in a two-minute CPR timer (approx. 16.5% progress). Accordingly, the visual progress indicator supplements the timer display because it shows not only elapsed time, but also provides an indication of elapsed time relative to the end of a cycle time interval, because the end point of the cycle is not apparent from the display of elapsed time alone. FIGS. 5 and 6 show additional progress towards the end of the two-minute cycle of the CPR timer. This arrangement contributes to display of information in a particularly compact form.

In this example, exemplary visual progress indicators are progress bars, and in particular, circular progress bars. Accordingly, these exemplary progress bars are in a shape defining an internal area. Preferably, the progress bar corresponding to an associated cycle timer are displayed via the display such that each task timer is displayed within a respective internal area of a respective one of the visual progress indicators. This may be performed by the DE 170 and/or IM 150. This arrangement contributes to display of information in a particularly compact and information-dense form.

Figure 7:
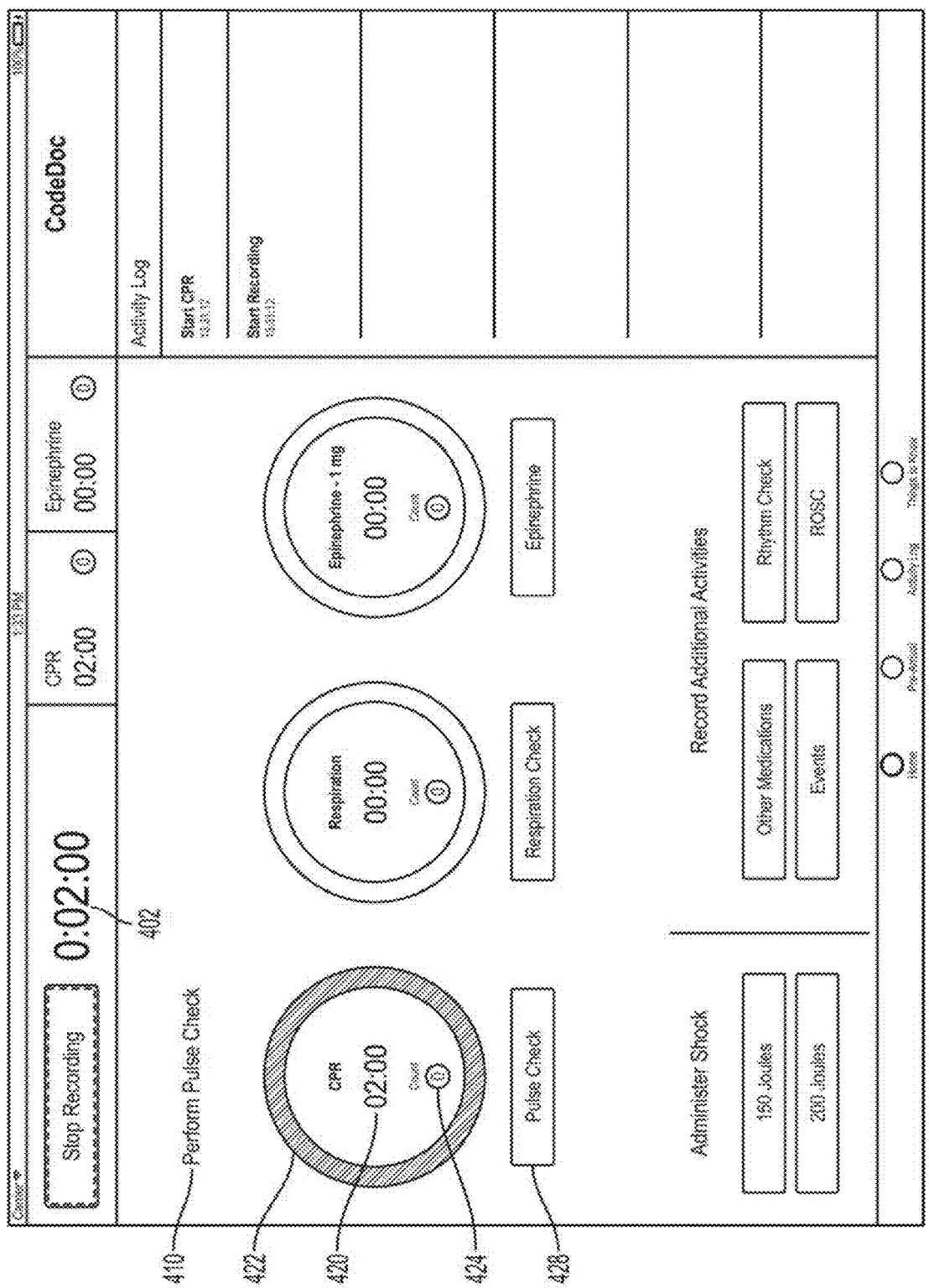

Referring again to FIG. 3, the method next involves determining whether a cyclical task timer has expired, as shown at step 314. This is performed by the IE 150. If not, the method flow continues in a continuing loop as shown in FIG. 3, and the timers continue to run. FIG. 7 shows two minutes of elapsed time in the session timer, as well as two minutes of elapsed time on the CPR timer 420. Additionally, FIG. 7 shows via the visual progress indicator 422 that two minutes is a completed CPR task cycle. Optionally, the DE 170 may cause the visual display indicator or another portion of the window 400 to change color (e.g., from blue to red) to provide a further indication that a task time interval cycle has been completed and that signals to the user/healthcare provider that action is required. This contributes to display of information in a particularly compact and information-dense form. These displays are controlled by the DE 170. If it is determined that a cyclical task time has expired at 314, then method flow continues to 316.

As shown in FIG. 3, the exemplary method next involves display of at least one task-specific guided instruction sequence, such as a plurality of related instructions, in accordance with the predetermined care protocol as defined in the CPDS 180, as shown at 316. The instructions may be based upon branched logic in accordance with the care protocol, such that at least one instruction is selectively displayed in response to prior user input provided in response to a prior displayed instruction. By way of example the textual instruction may be a textual instruction to perform a medical care task, or to provide specific data input to the care support system via the user input component. This may be performed by the DE 170 under control of the IE 150. In this example, this step is performed as a function of elapsed time, as defined in the CPDS 180, and involves display of a PERFORM PULSE CHECK message 410 within the window 400. This prompts the performance of a pulse check care action, in which a healthcare provider checks the pulse of the patient in distress. The operator of the CSS 100 can initiate pulse check logging functionality by selecting an associated PULSE CHECK button 428 displayed within the window 400, as shown in FIG. 7. In this manner, the system and method controls the interface to deliver structured guidance to medical personnel during a medical emergency to promote rendering of medical care in compliance with predetermined care protocols.

Figure 8:
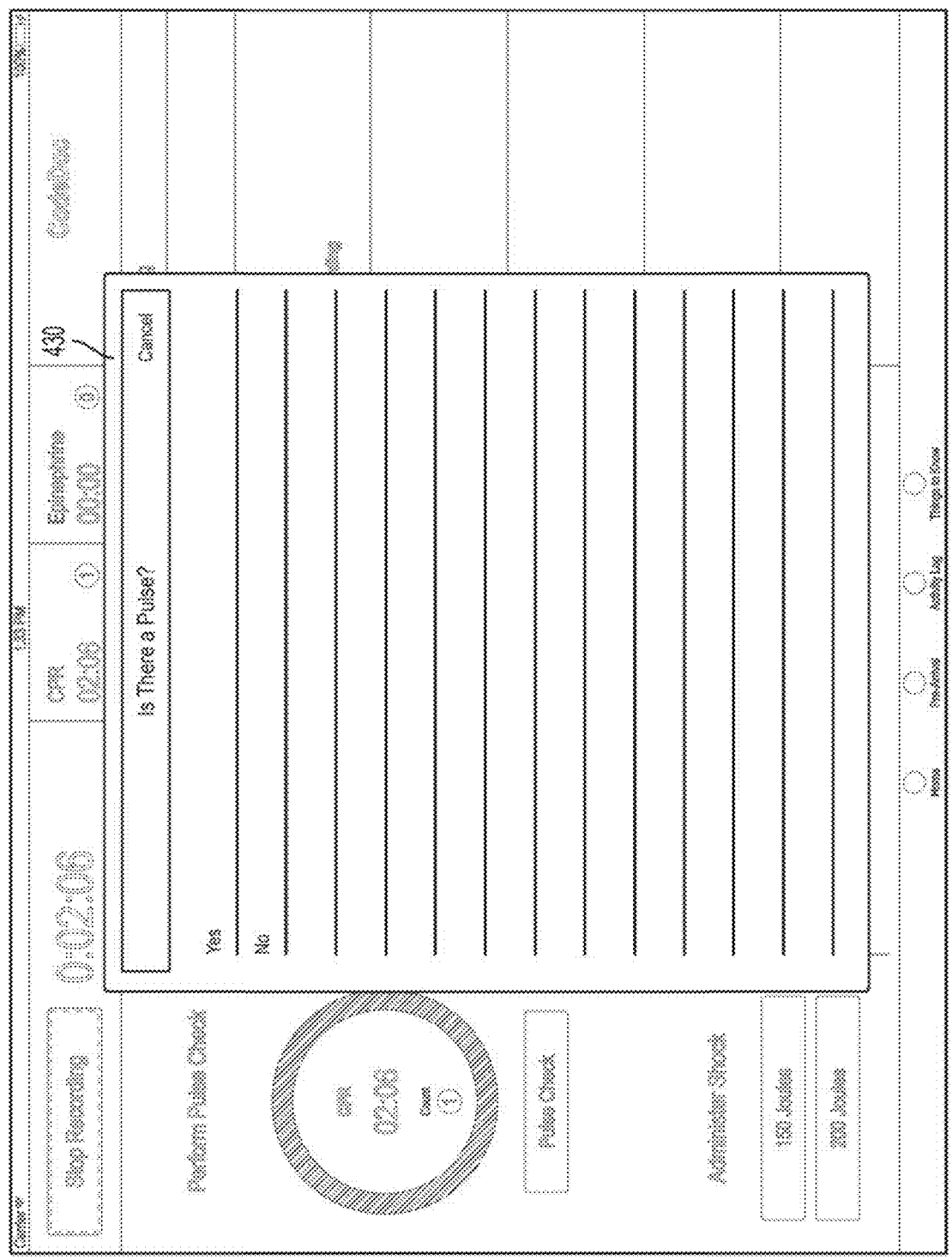
Figure 9:
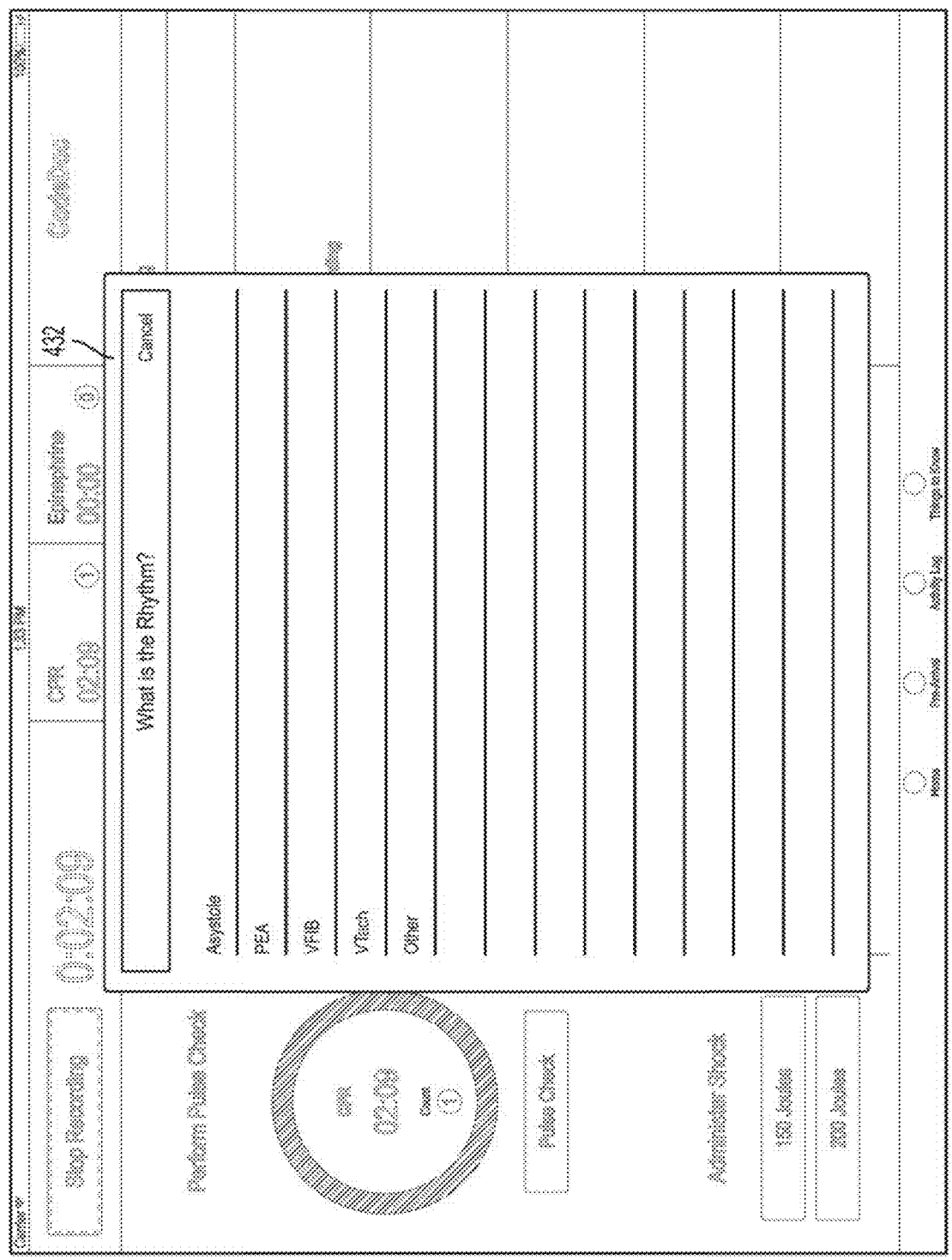
Figure 10:
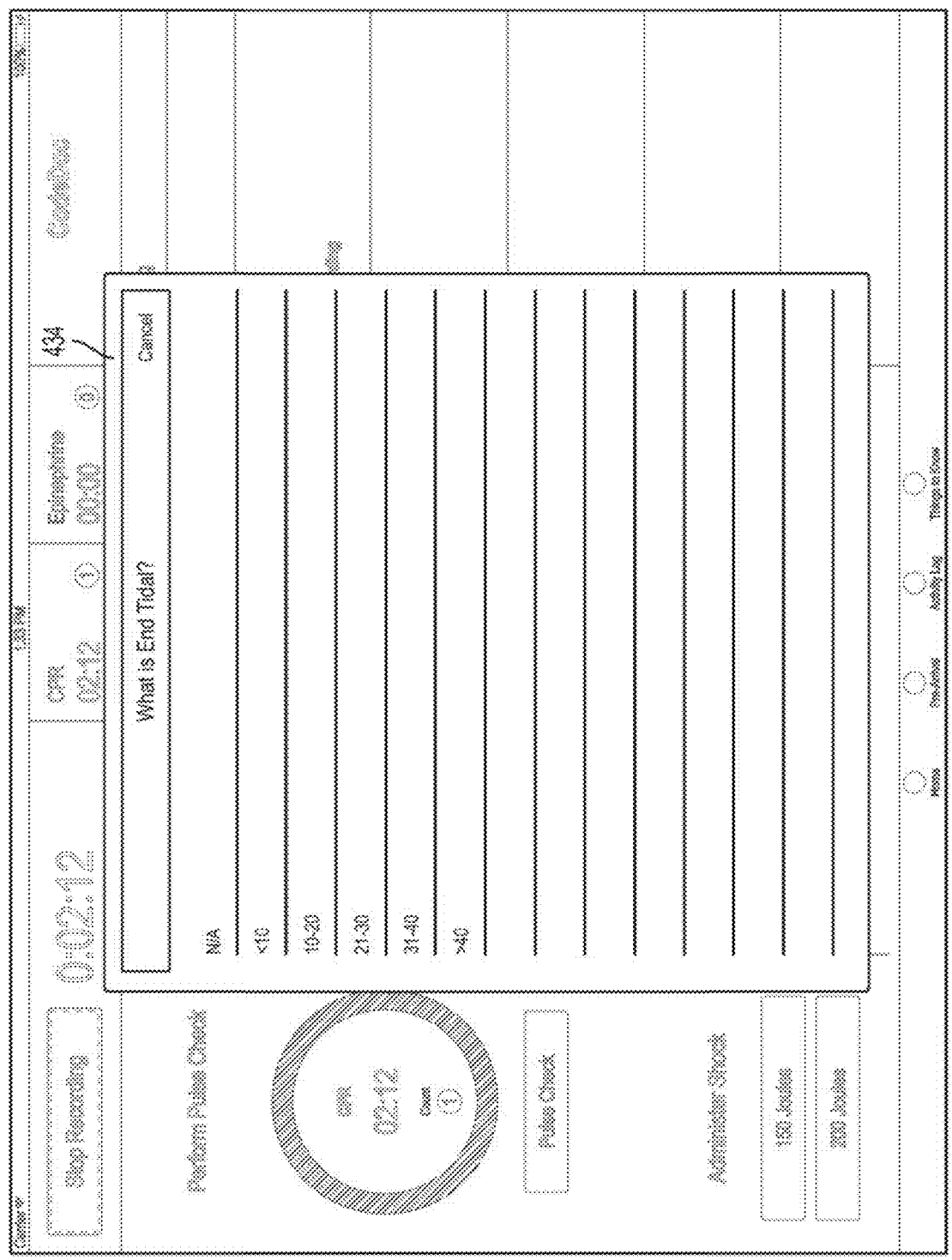

In accordance with predetermined logic and rules built into the IE 150, the DE 170 in this example then displays additional windows that convey information to the operator, prompt the healthcare provider to act, and/or prompt the operator to input information into the CSS. For example, a guidance window 430 is shown in FIG. 8 and is displayed in response to the operator's actuation of the Pulse Check button 428 in FIG. 7. This exemplary window queries whether the patient has a pulse, thereby prompting the healthcare provider to take the pulse of the patient in distress, and thereby prompting the user to input YES or NO via a menu displayed within the window 430. Notably, the display of this window and the prompting to take such action and gather information at this time is performed precisely because the AHA care protocol provides that this should be done at this time. Accordingly, the CSS is thereby providing guided instruction for compliance with the applicable care protocol. Additional windows may be displayed 432, 434, and additional data may be gathered, in accordance with the protocol, as shown in FIGS. 9 and 10. Once the appropriated guidance has been provided and information has been gathered in accordance with the protocol, this step ends. Optionally, the DE 170 may display textual or other prompts and/or may display menus of user-selectable input options, in accordance with branched logic defined in the CPDS 180. Accordingly, for example, prompts and/or menus of input options may be displayed, at least in part, in selective fashion, based on prior inputs provided to the system.

Figure 11:
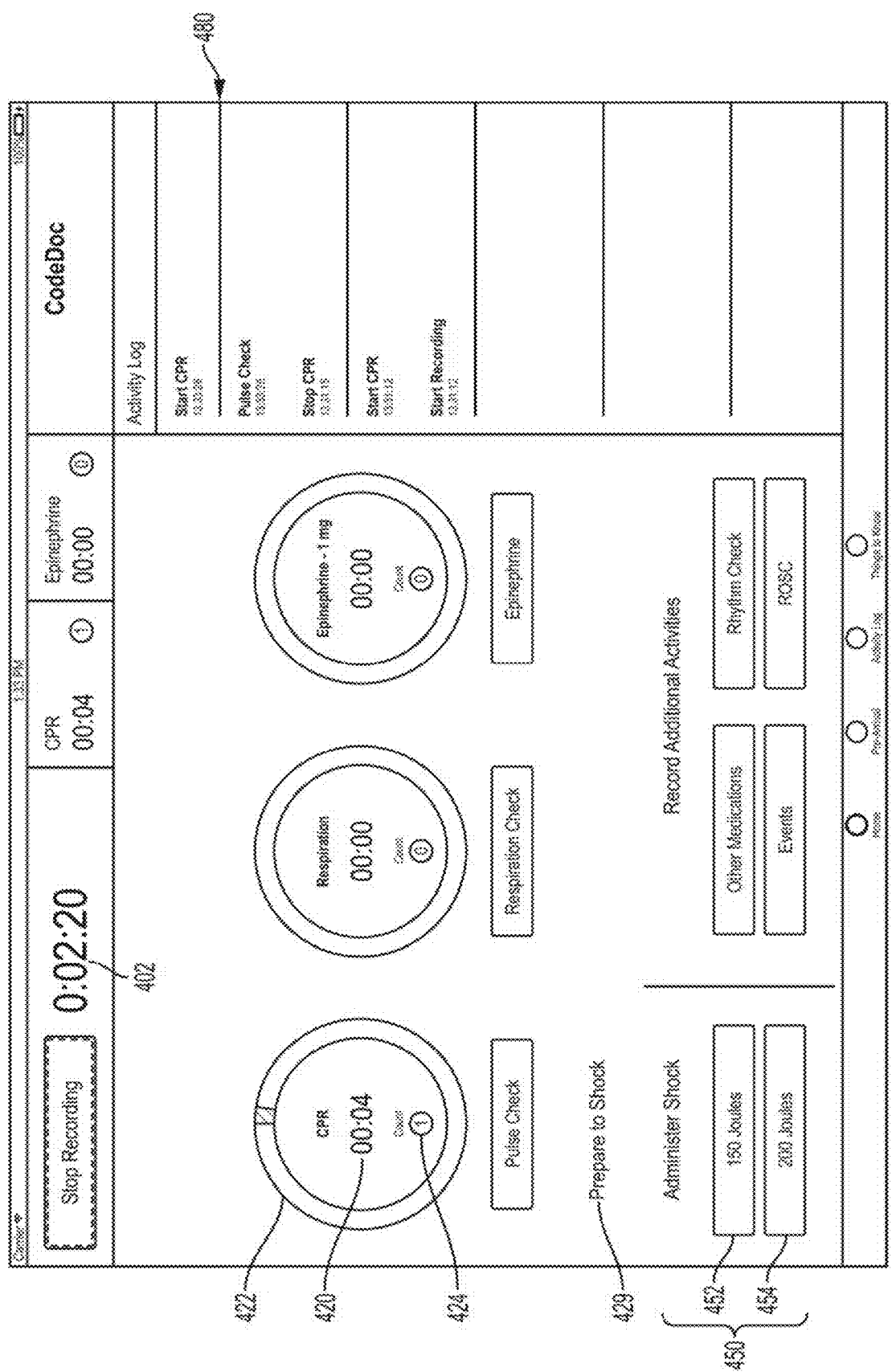
Figure 14:
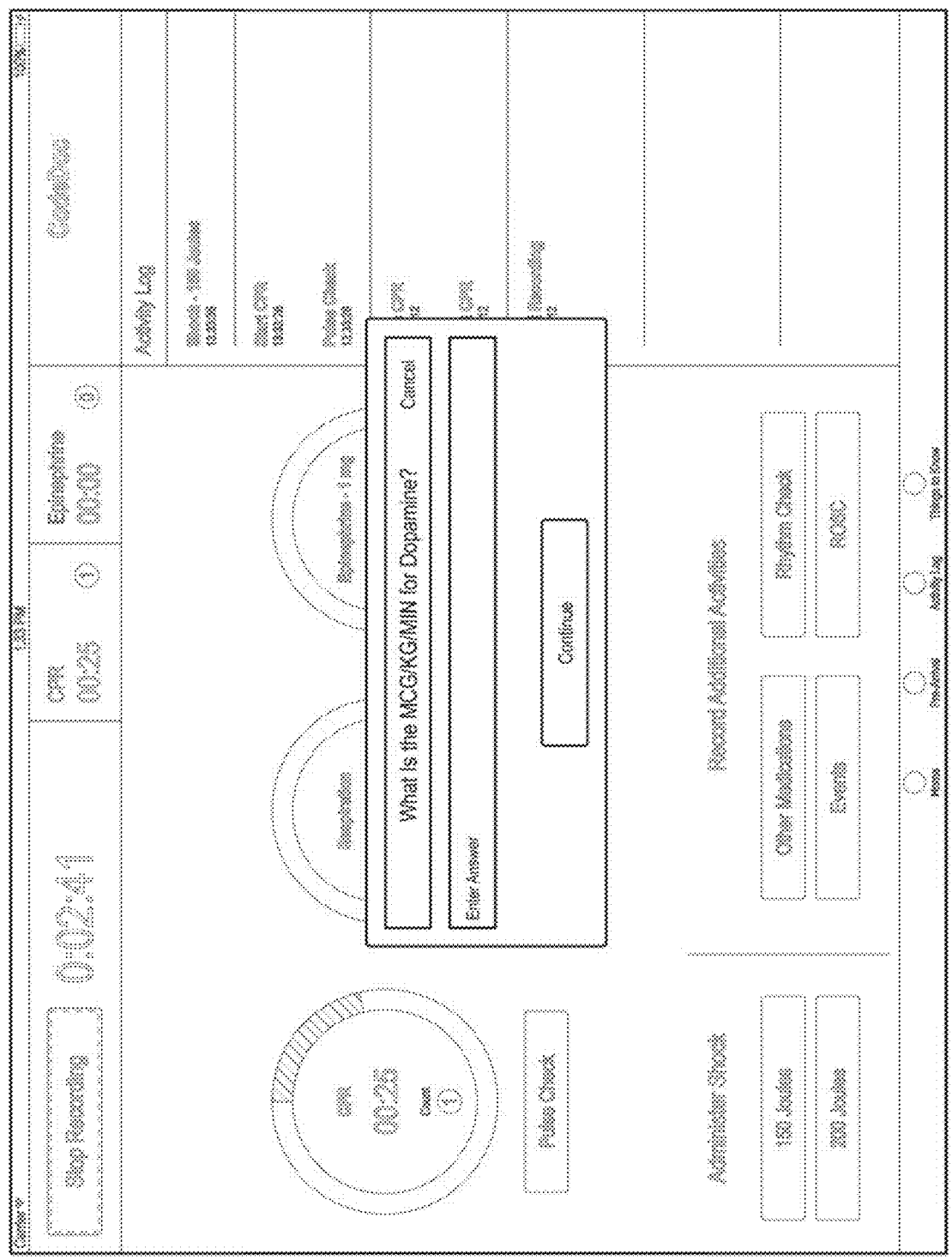
Figure 15:
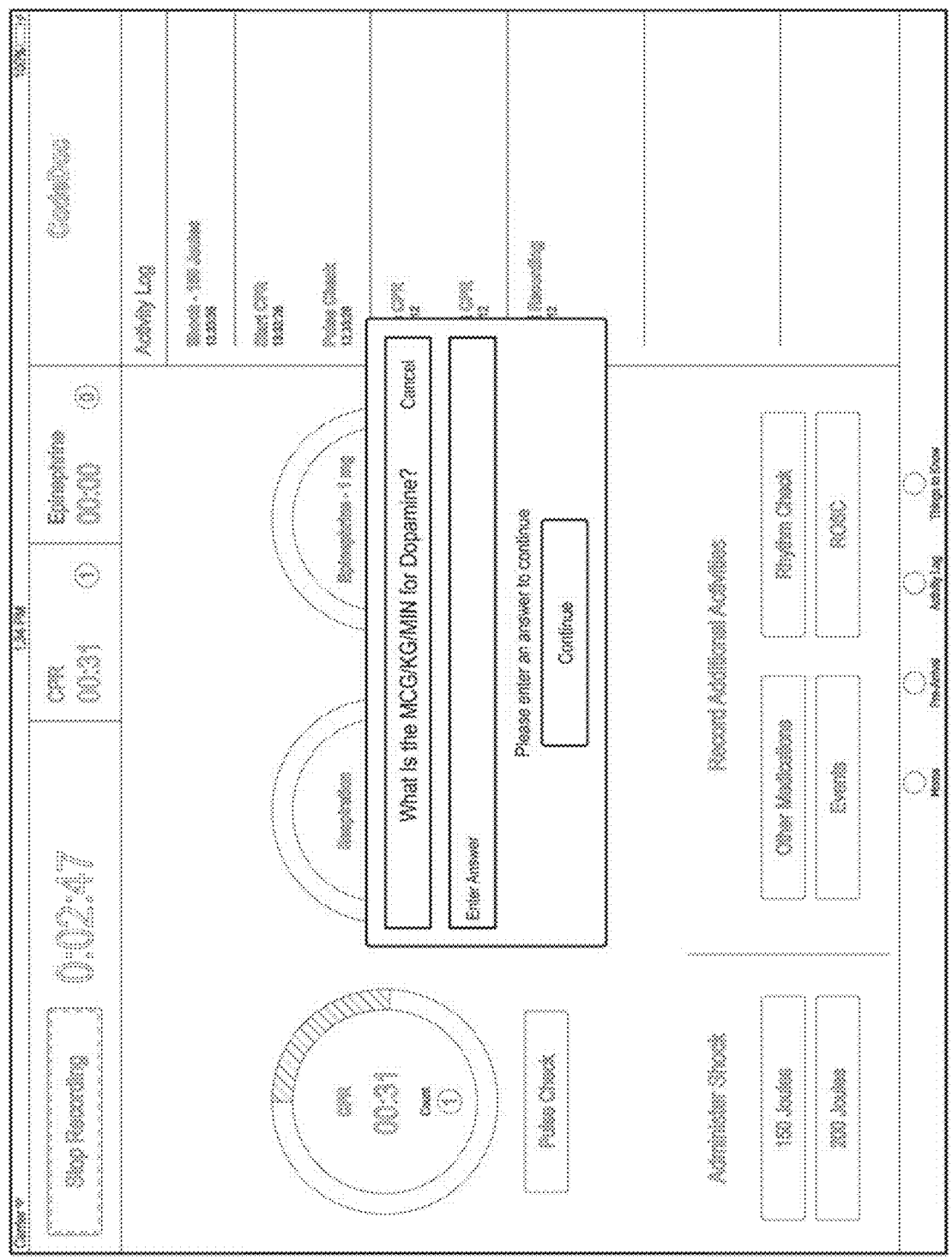
Figure 16:
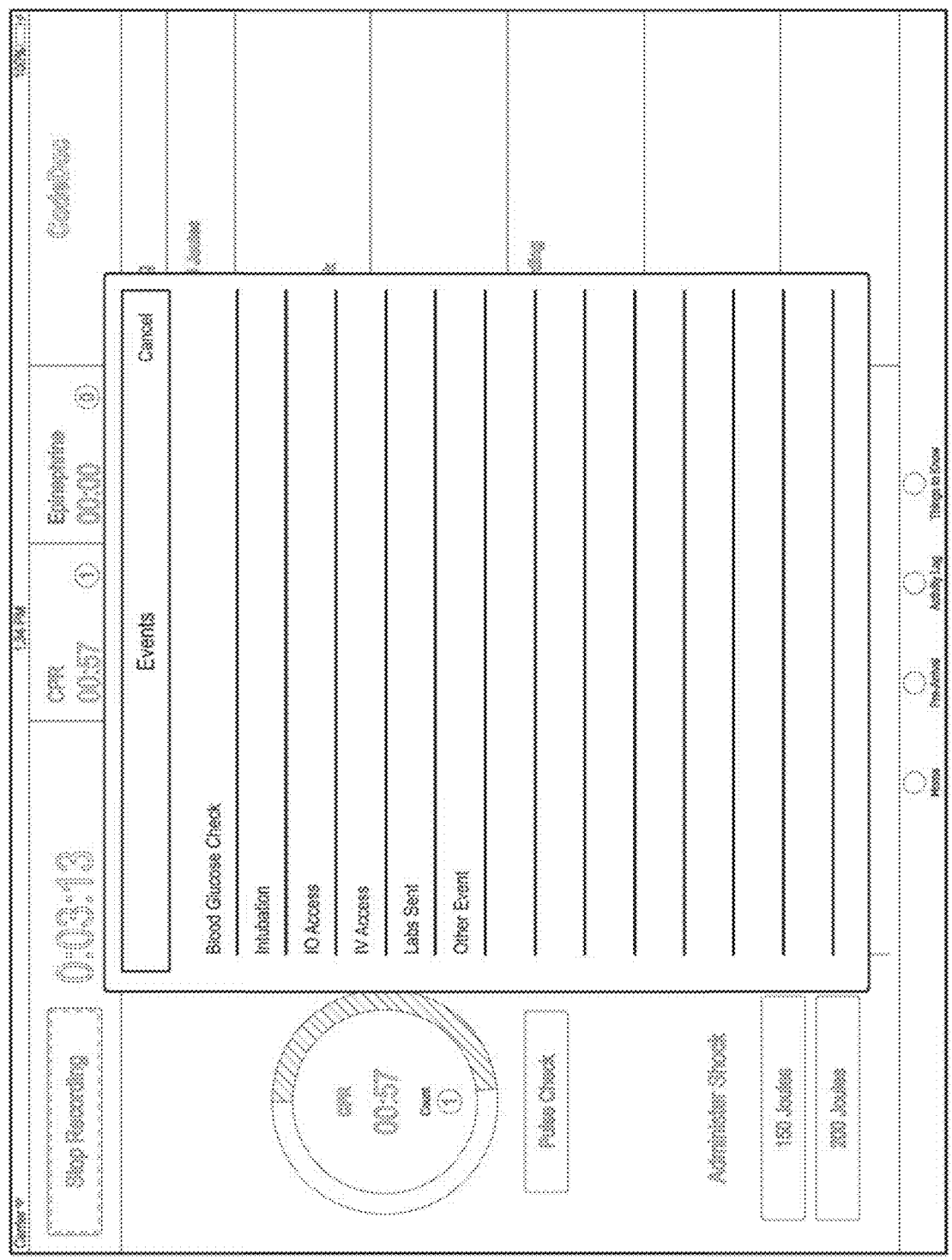
Figure 17:
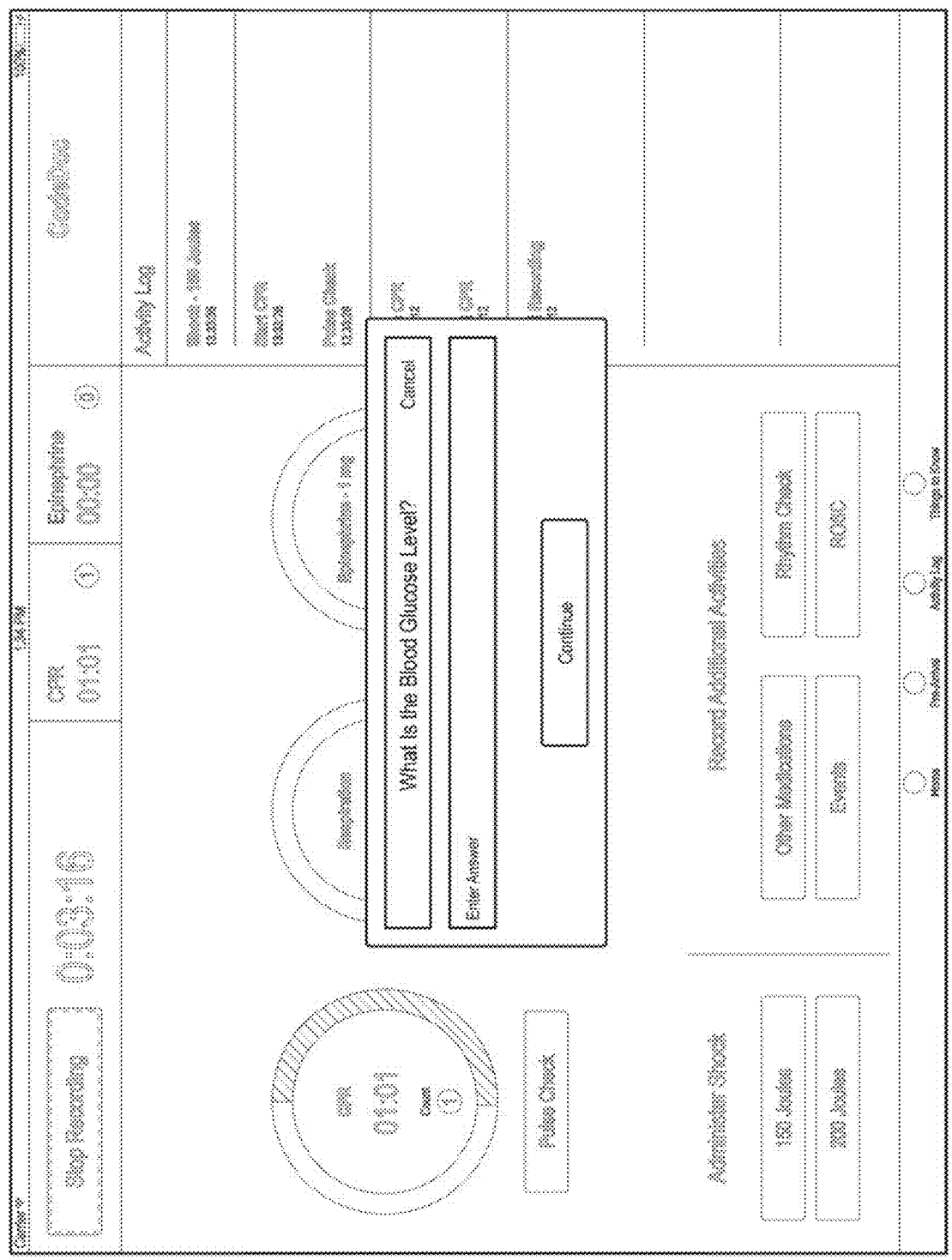
Figure 19:
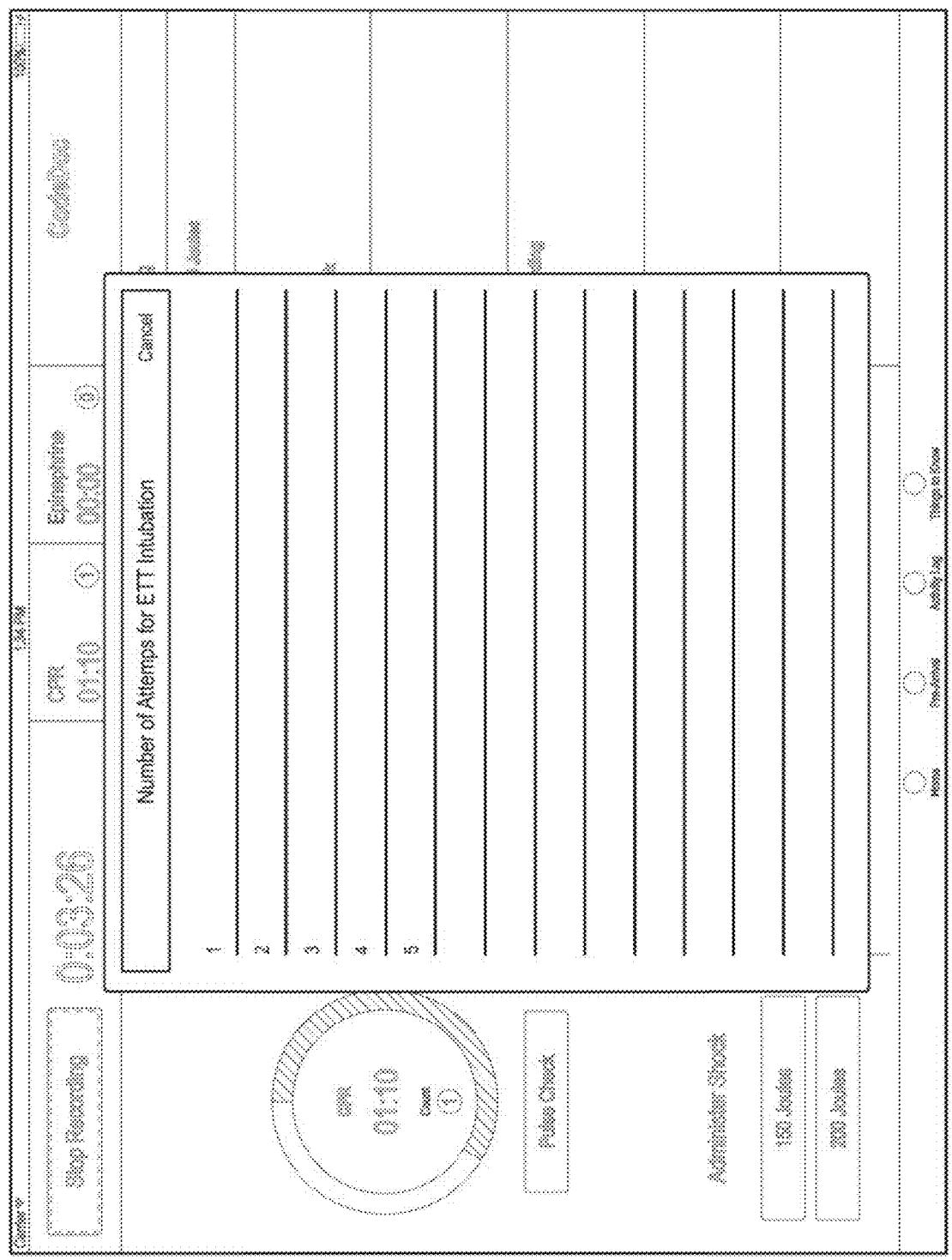
Figure 21:
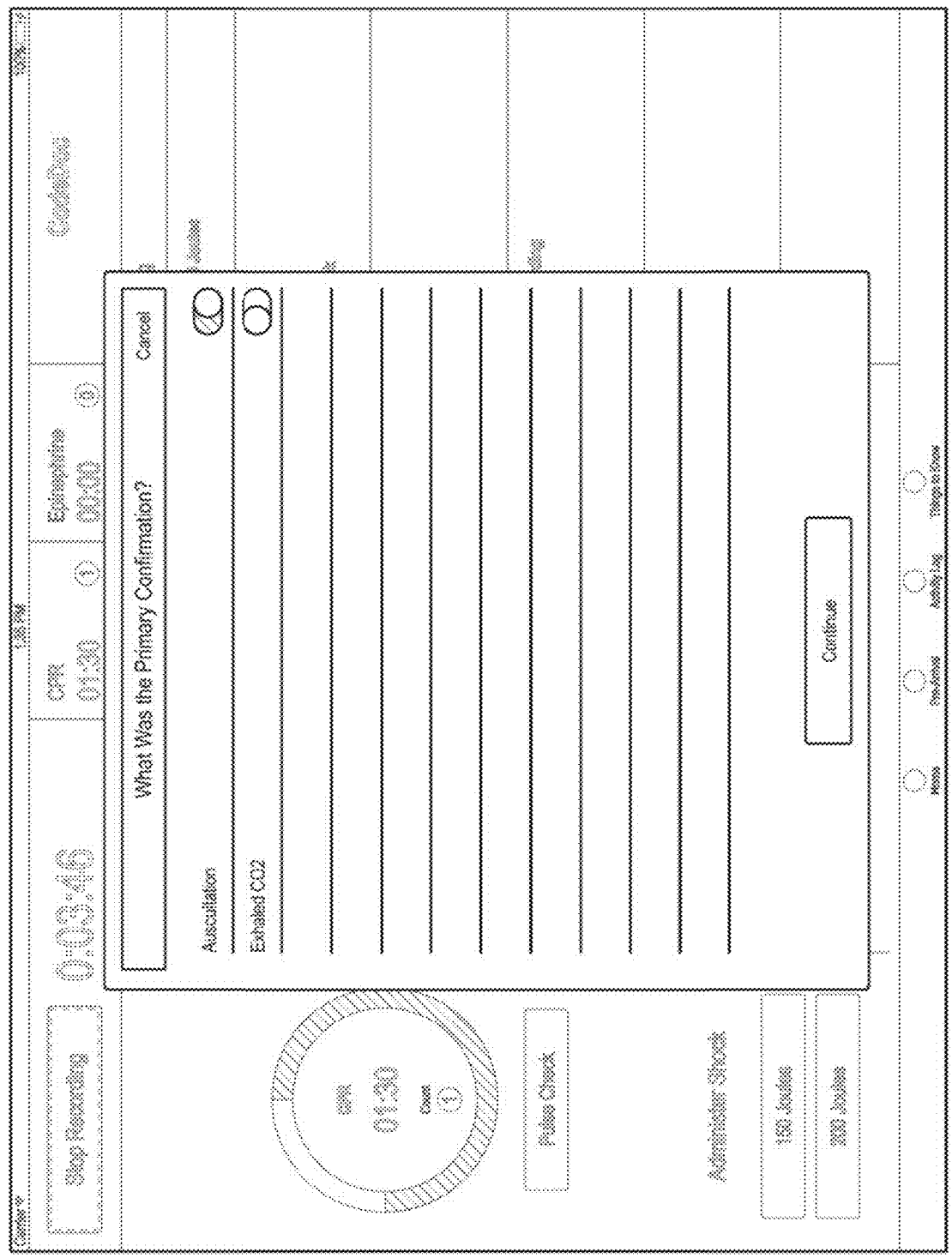
Figure 22:
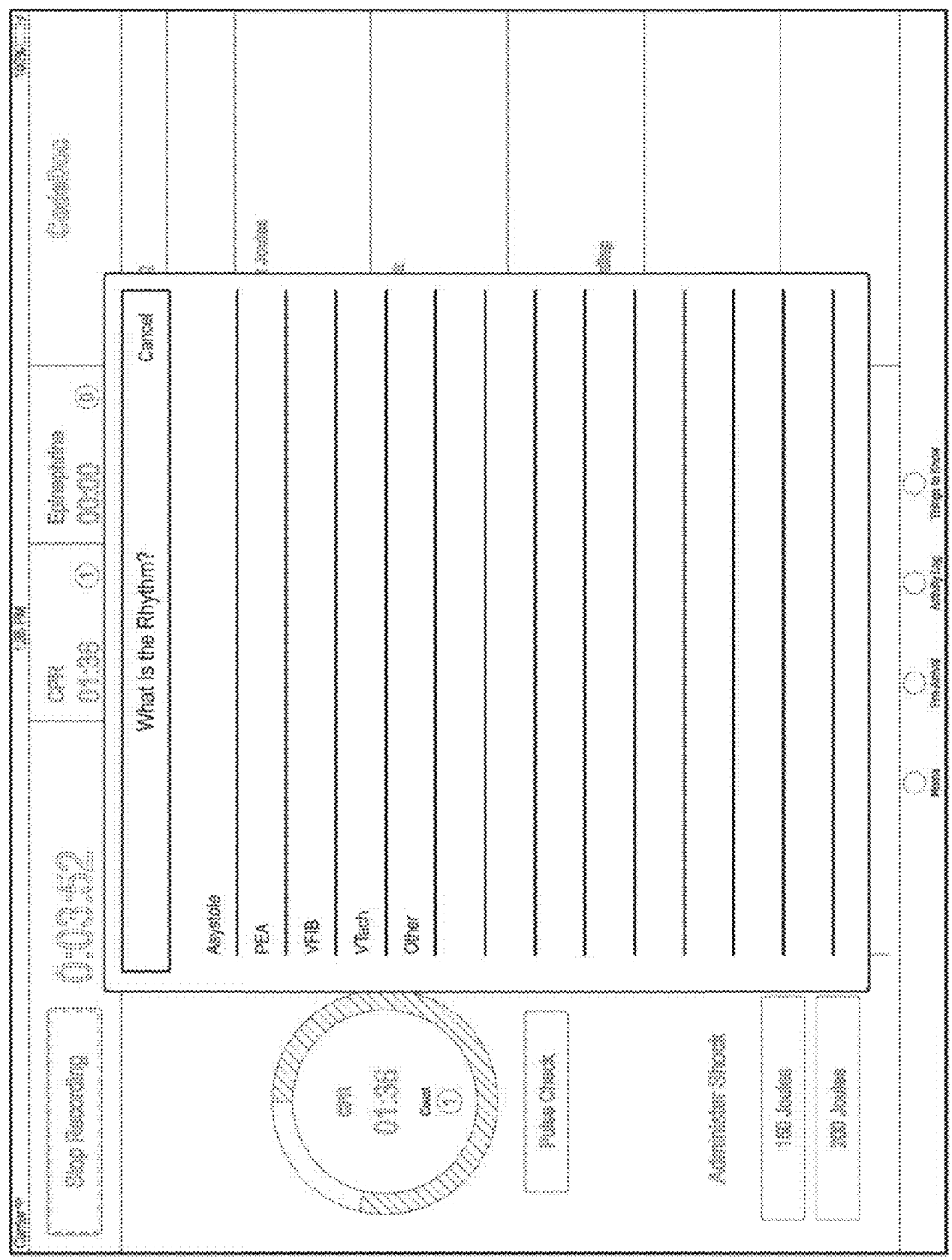
Figure 23:
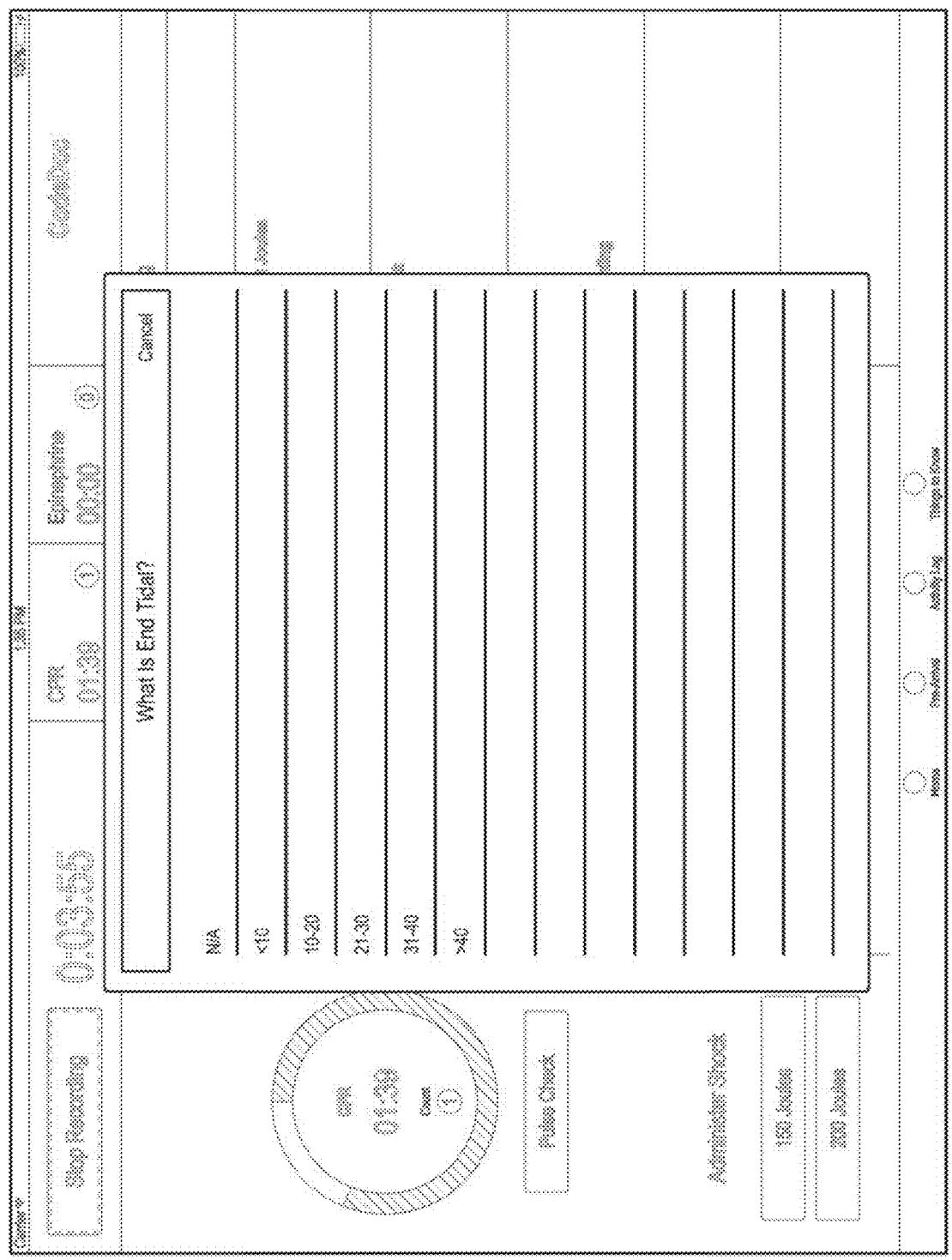
Figure 24:
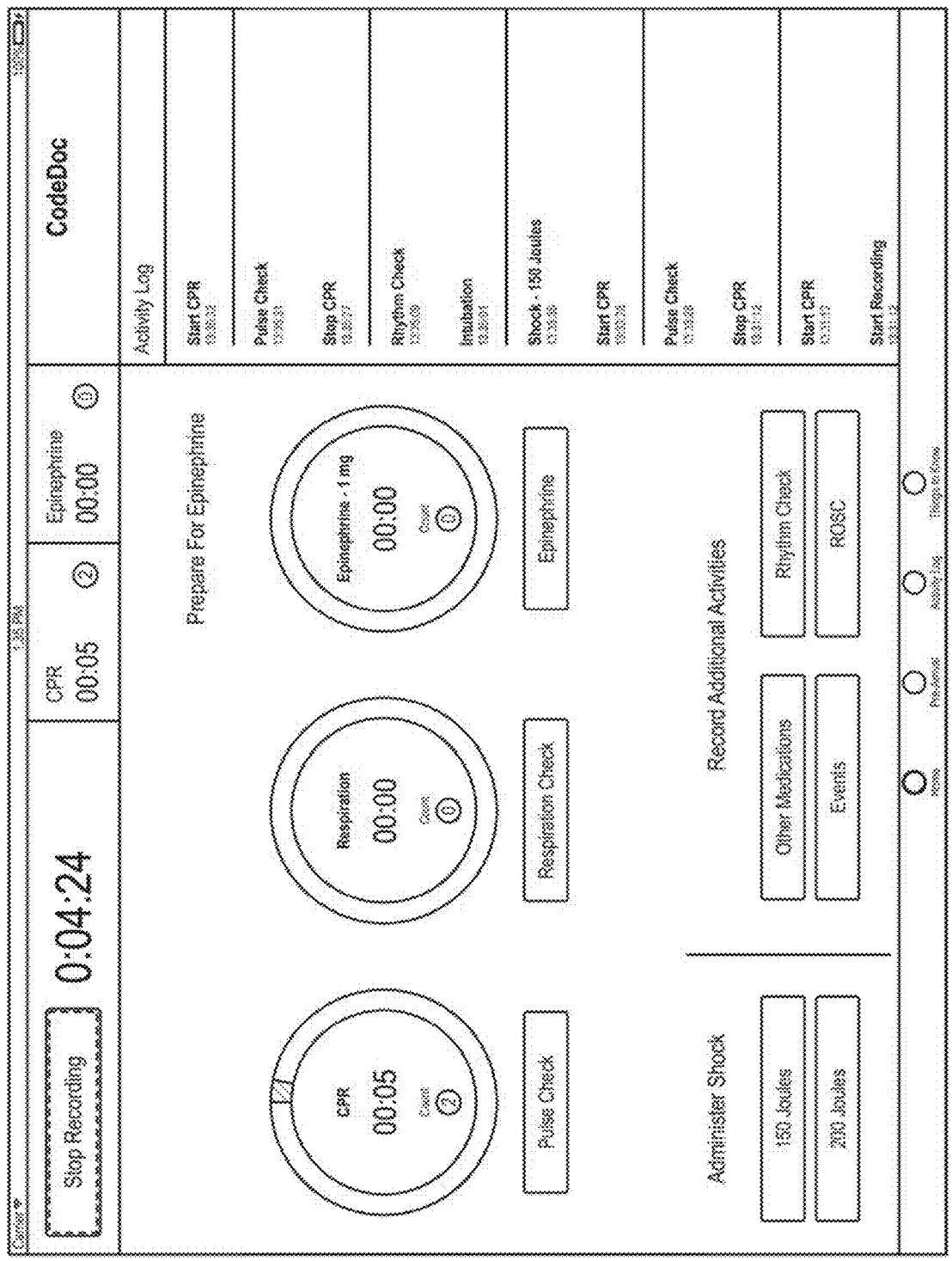
Figure 25:
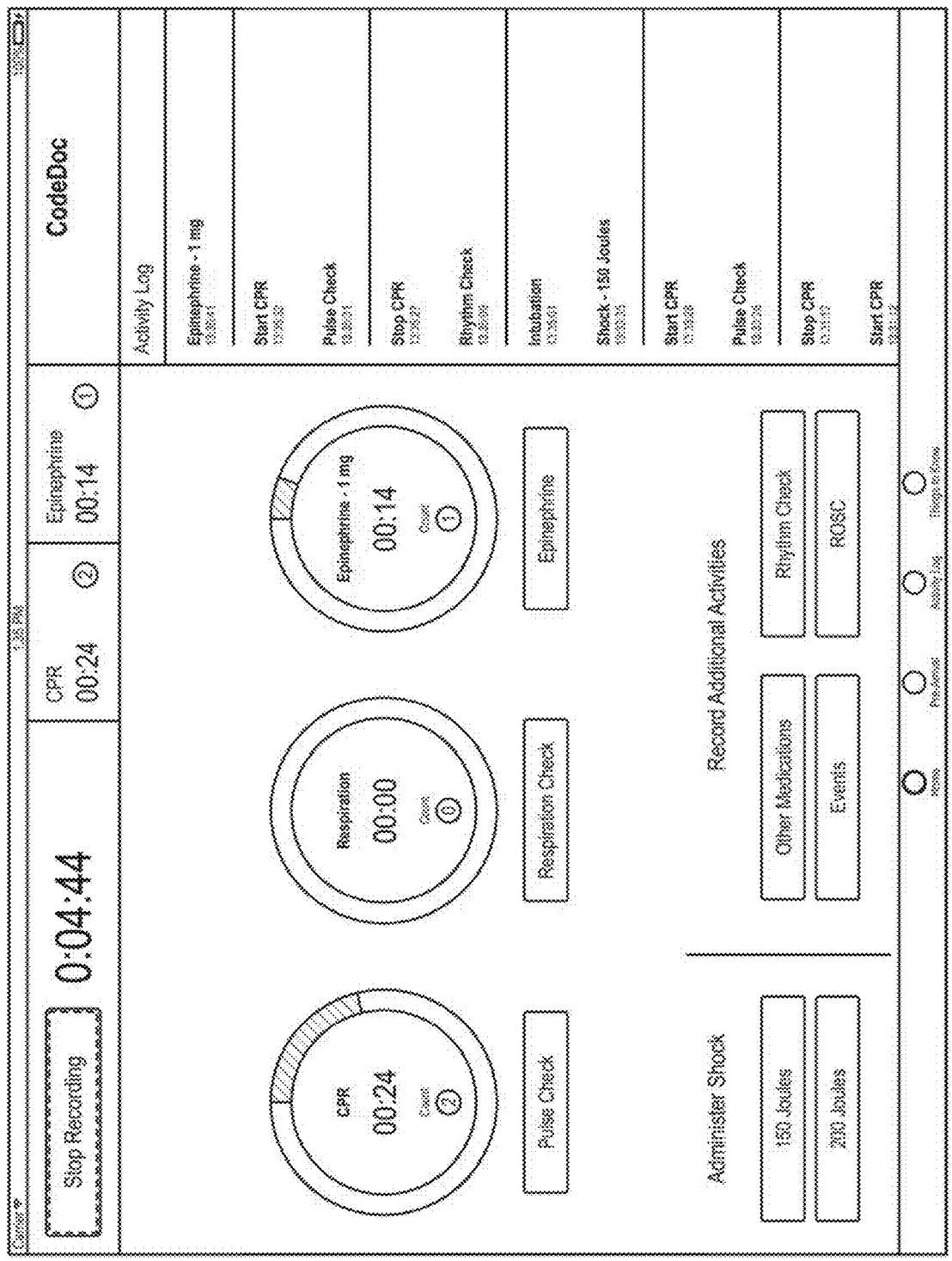
Figure 32:
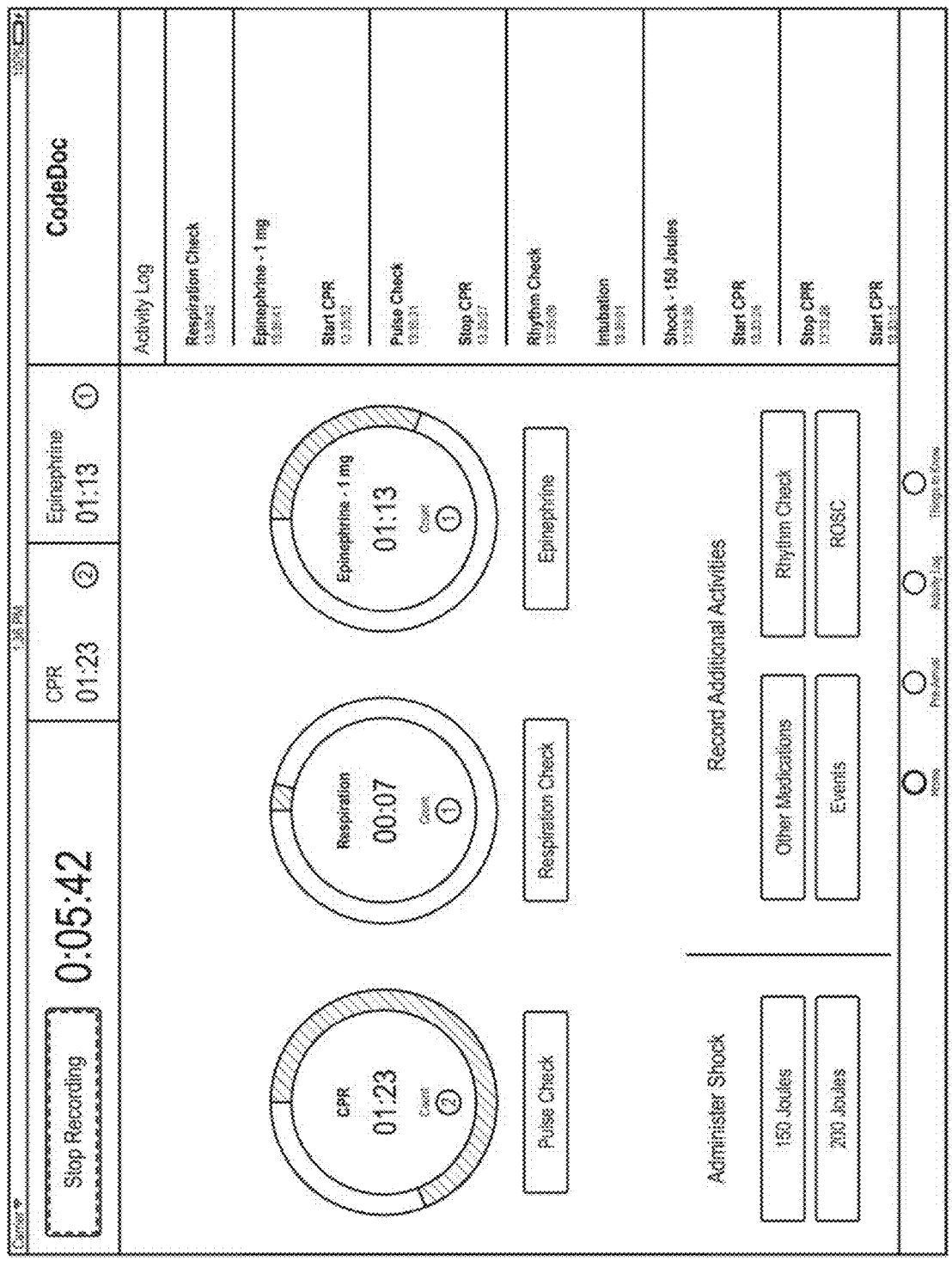
Figure 33:
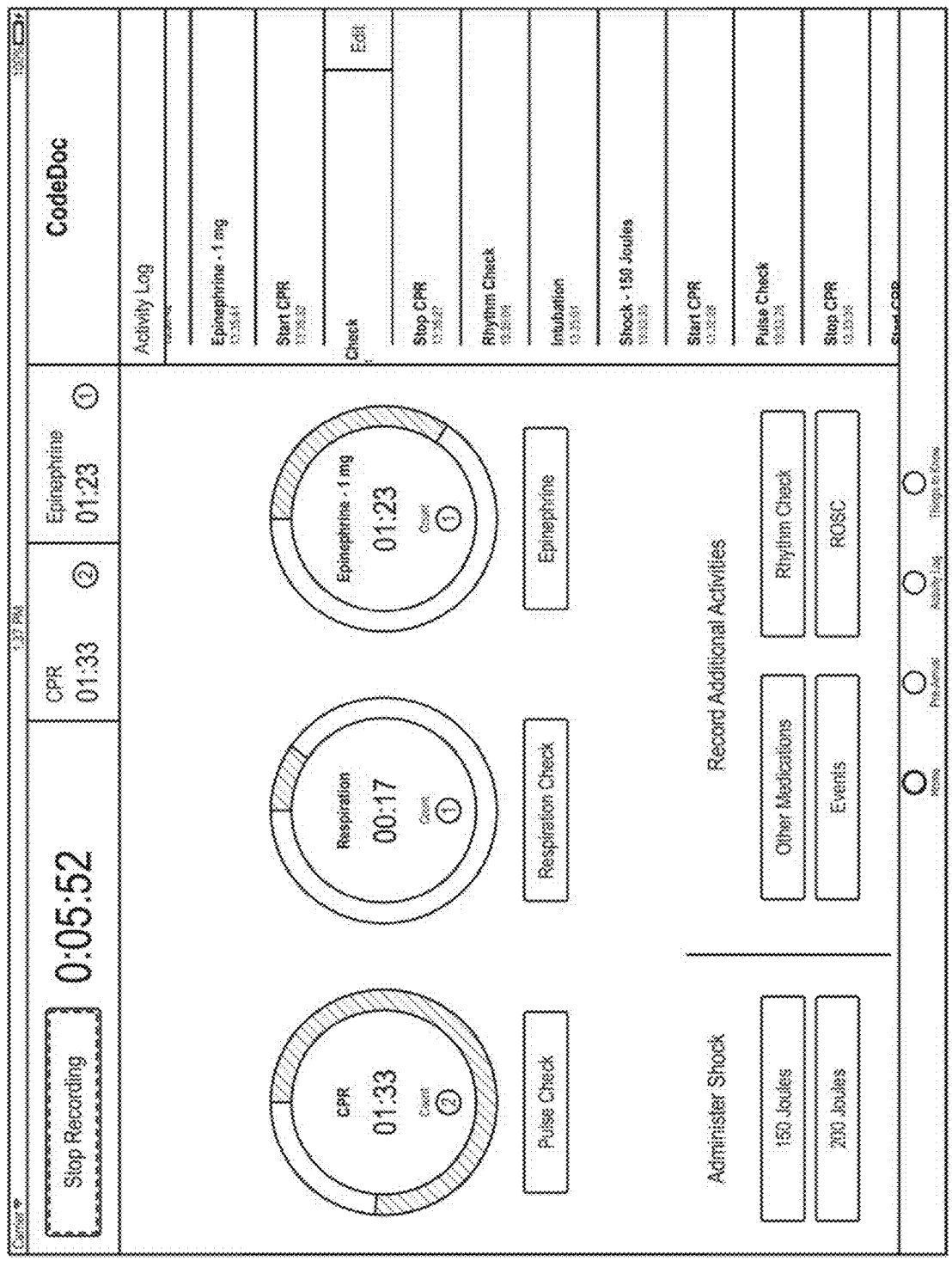
Figure 34:
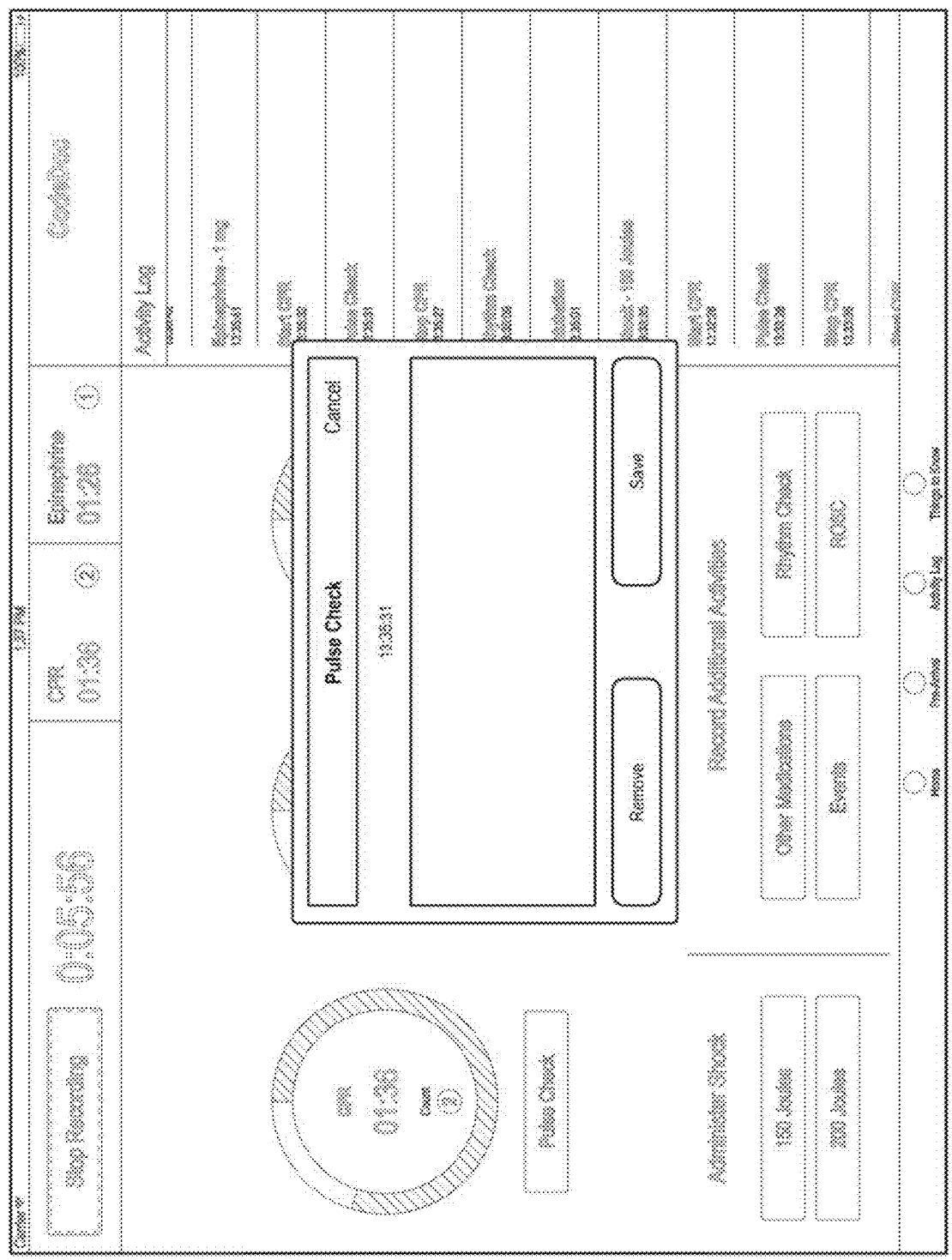
Figure 35:
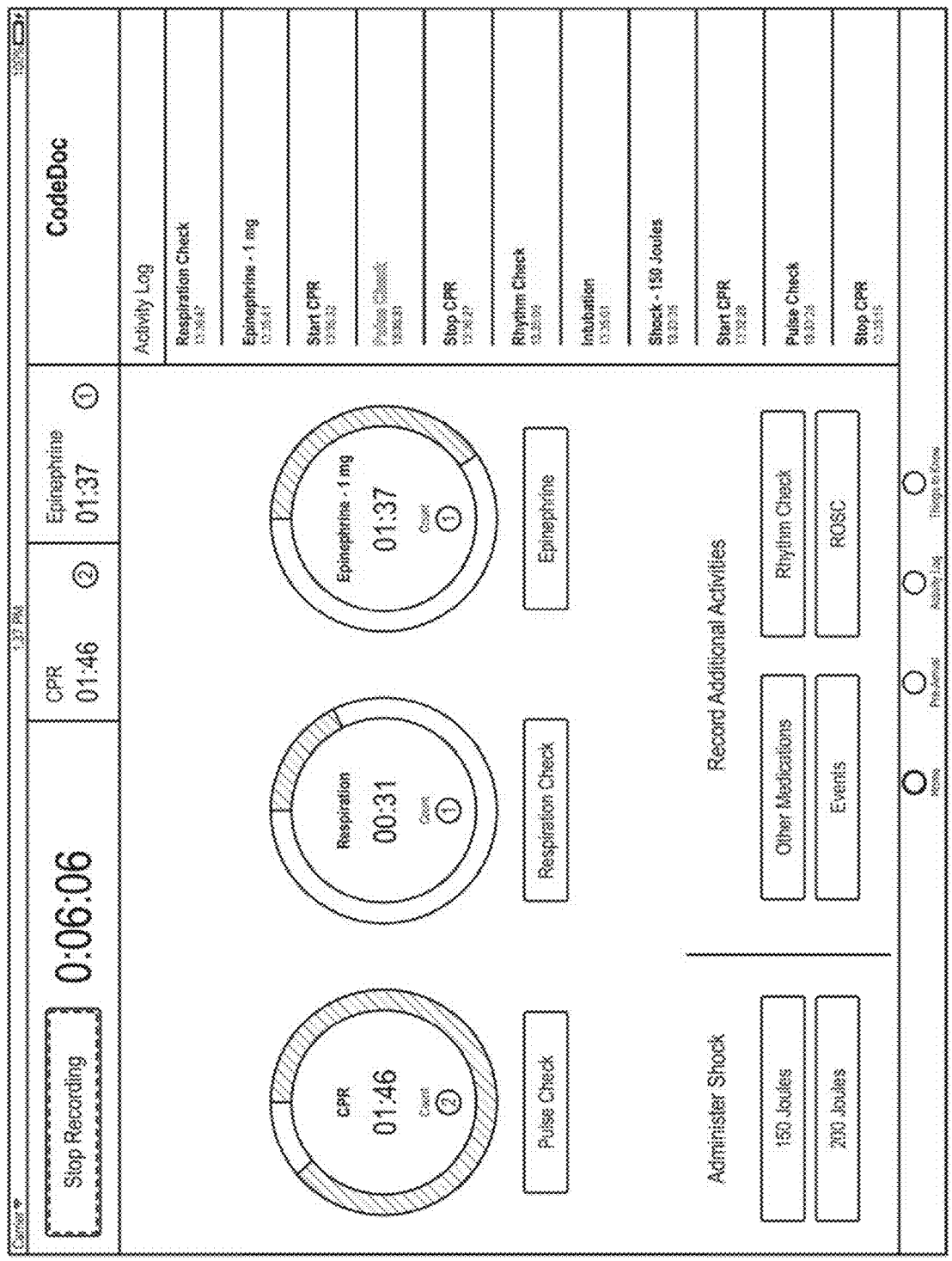

Accordingly, the method next involves augmenting a cycle counter for the associated task, storing user input, time data, and cycle count data, and displaying in the window 400 the augmented count in a counter 424 association with the associated task, as shown at 318, 320 and 322. This may be performed by the DE 170 and/or IM 150. FIG. 11 shows display of the augmented count (now 1, reflected 1 cycle has been completed) for the CPR task. This is shown by displaying the count adjacent to the CPR timer, or progress bar, or otherwise within a common subfield of the window 400, as shown in FIG. 11. In a preferred embodiment, the DE 170 and/or IM 150 displays each cycle counter within a respective internal area of a respective one of said plurality of visual progress indicators. This arrangement contributes to display of information in a particularly compact and information-dense form.

Next, the exemplary method involves resetting and restarting the cyclical task timer, as shown at 324, and this involves display of a reset timer and visual progress indicator, which may be performed by the DE 170. This may be performed automatically in response to expiration of a timer, or completion of a certain task and/or providing of associated input to the system. FIG. 11 shows 4 seconds of elapsed time on the CPR timer 420 after the restart, and a corresponding amount of progress on the associated visual progress indicator 422. Due to the time it took to provide input in response to the guidance windows 430, etc., the two-minute CPR interval timer is no longer in synch with the free-running session timer. In another embodiment, the two-minute CPR timer remains synchronized with the free-running session timer until it gets reset manually. At this time, a "count" or "counter" is augmented for the timer, such that the counter reflects the number of cycles (either completed or including the cycle in progress) for each particular timer. This is performed by the DE 170, and the counter is displayed in proximity to its associated timer (either numerical timer or visual progress indicator). This arrangement contributes to display of information in a particularly compact and information-dense form. In one embodiment, the progress indicator defines an internal area bounded by the progress bar, and one or both of the associated numerical timer and counter are displayed within the area defined by the progress indicator. This arrangement contributes to display of information in a particularly compact and information-dense form.

If the user has not ended the session, then method flow returns to 314, where it is again determined whether a cyclical task timer has expired, and the method continues in similar fashion. The Respiration Check and Epinephrine delivery timers work in similar fashions, as can be appreciated from FIGS. 32-33. This may proceed for numerous cycles for each of the CPR, Respiration Check and Epinephrine delivery tasks. FIGS. 32-35 show elapsed time and progress for each of the CPR, Respiration Check and Epinephrine delivery tasks.

In this exemplary embodiment, additional guidance may be provided in accordance with the protocol, or otherwise. For example, FIG. 11 shows that the IE 150 is displaying a message 429 guiding the operator and/or healthcare provider to PREPARE TO SHOCK the distressed patient. This may be selectively displayed in accordance with predetermined logic, under control of the IE 150 and in accordance with the relevant care protocol, e.g., as a function of user input provided via the windows 430, etc. during the Pulse Check task. The window may provide a menu 450 of user-selectable options 452, 454 in accordance with the protocol (e.g., option 1 452 of 150 Joules, and option 2 454 of 200 Joules). The user may select one of these buttons to provide data entry as to the nature of the shock delivered to the patient. The Logging Engine 190 requires this data input, including associated time of delivery, and stores it in the memory 118. By way of example, the LE 190 may act in concert with the DE 170, so that a recording session cannot be closed/completed and/or a new recording session cannot be opened/started, until all required information has been input to the system/device and captured by the Logging Engine 190. The automated logging by the system 100, and the required logging imposed by the Logging Engine 190, contribute to the accurate and complete logging of information in accordance with prescribed protocols, guidelines and/or procedures.

Figure 29:
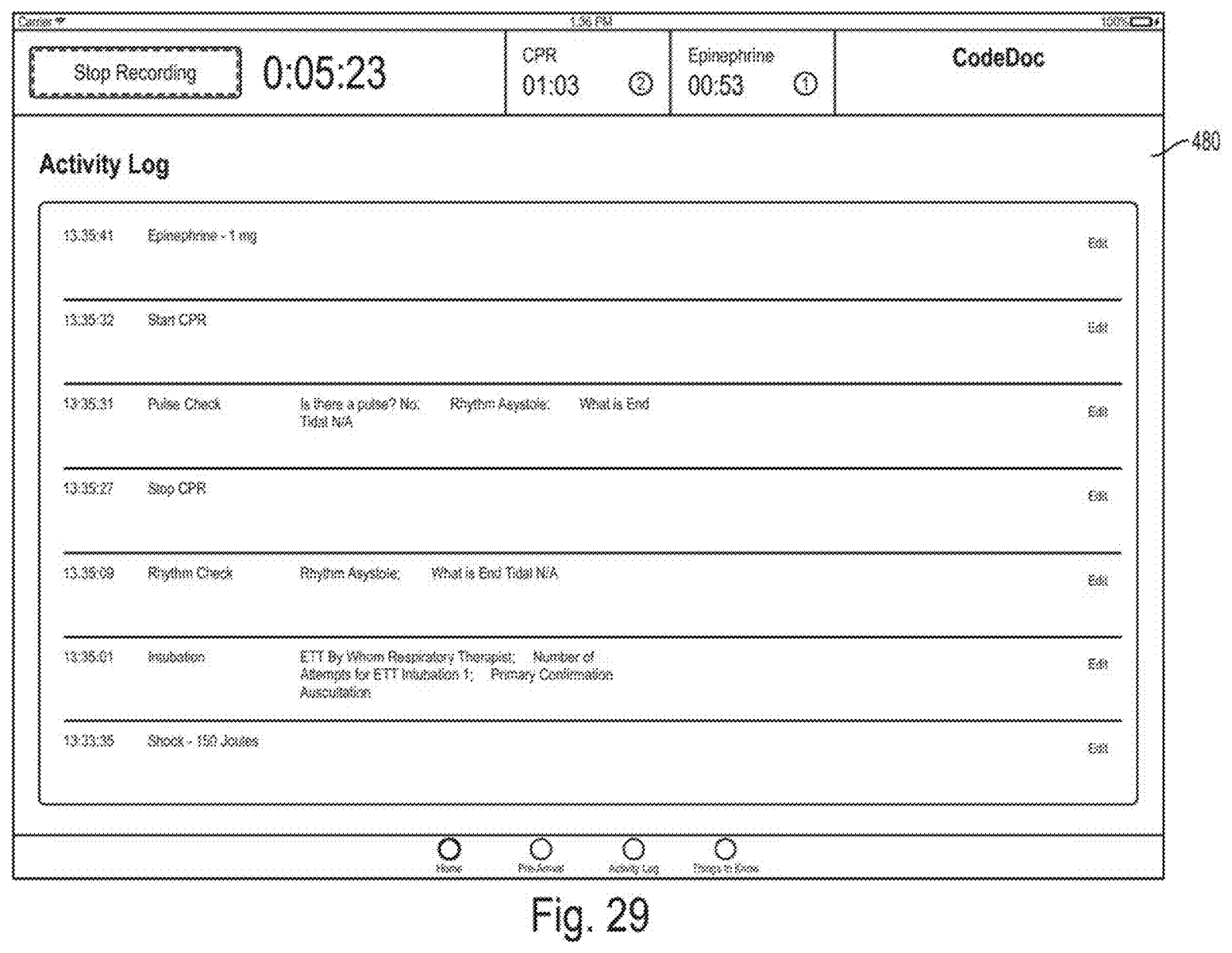

Information in the nature of an activity log, including descriptions of occurrences and timing of those occurrences, may be displayed by the DE 170 in a continuing Activity Log 480 displayed in scrolling fashion within a limited portion of the display, as shown in FIGS. 11 and 29. This arrangement contributes to display of information in a particularly compact form.

Similar functionality may be provided that is not a function of time, e.g., functionality, user-selectable options, and associated display of prompting and data-gathering windows to record additional information/activities—e.g., Other Medications, Events, Rhythm Check, Return of Spontaneous Circulation (ROSC), etc. FIGS. 12-23 show exemplary windows for prompting the operator to provide additional input to be recorded by the LE 190.

Figure 30:
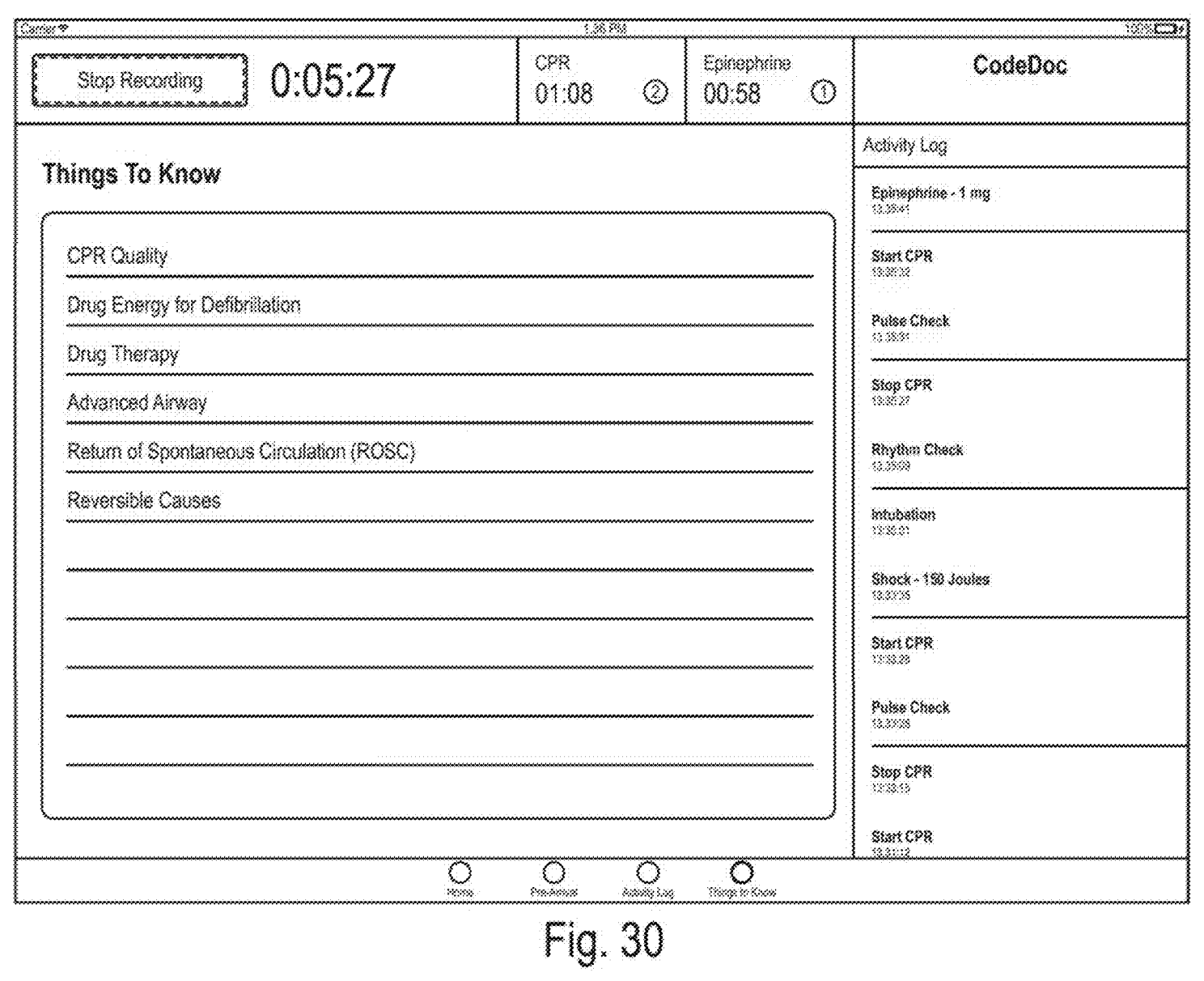
Figure 31:
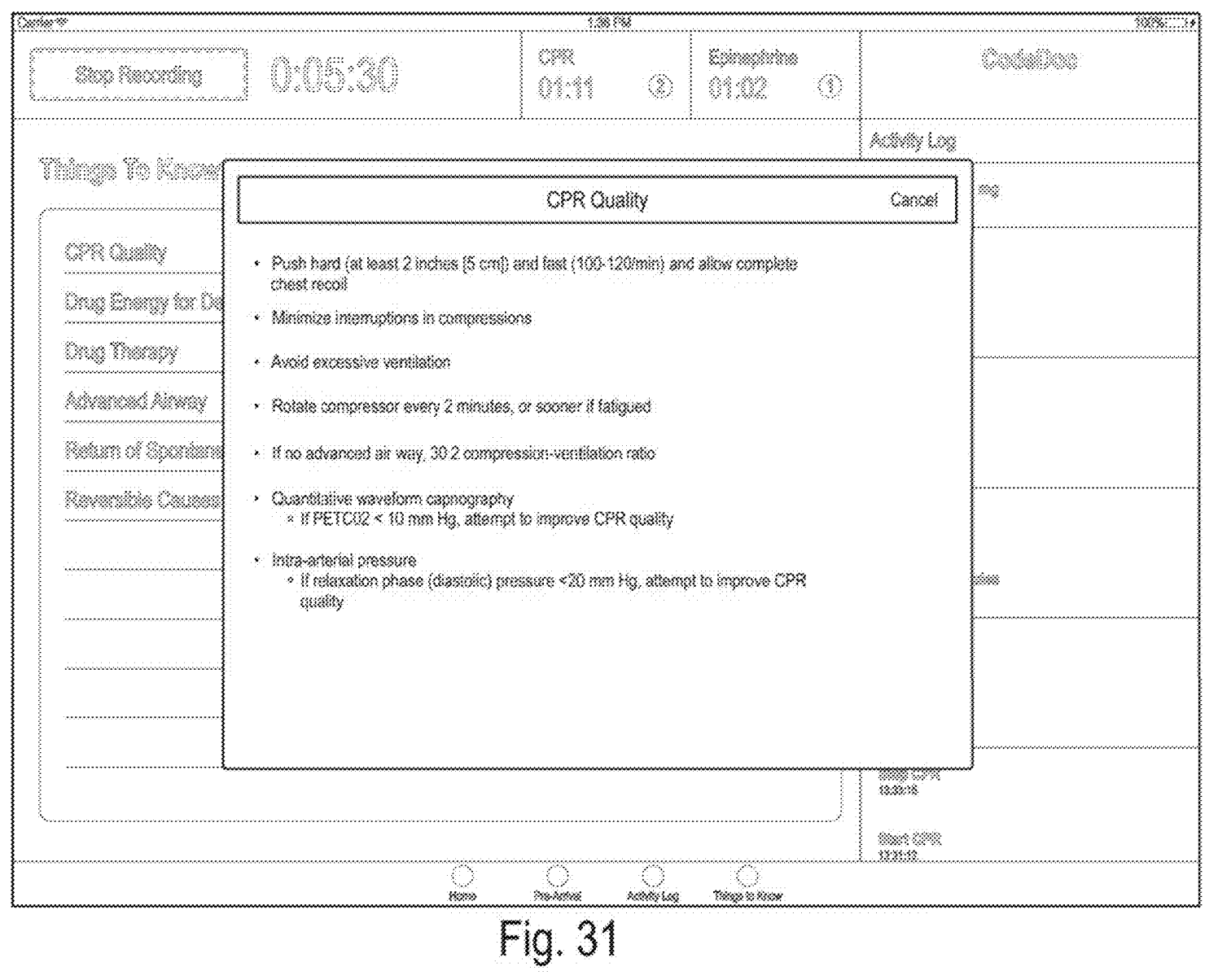

The system may further provide reference materials that may be accessed by the operator, e.g., to provide general reference information, as shown in FIGS. 30 and 31.

Figure 36:
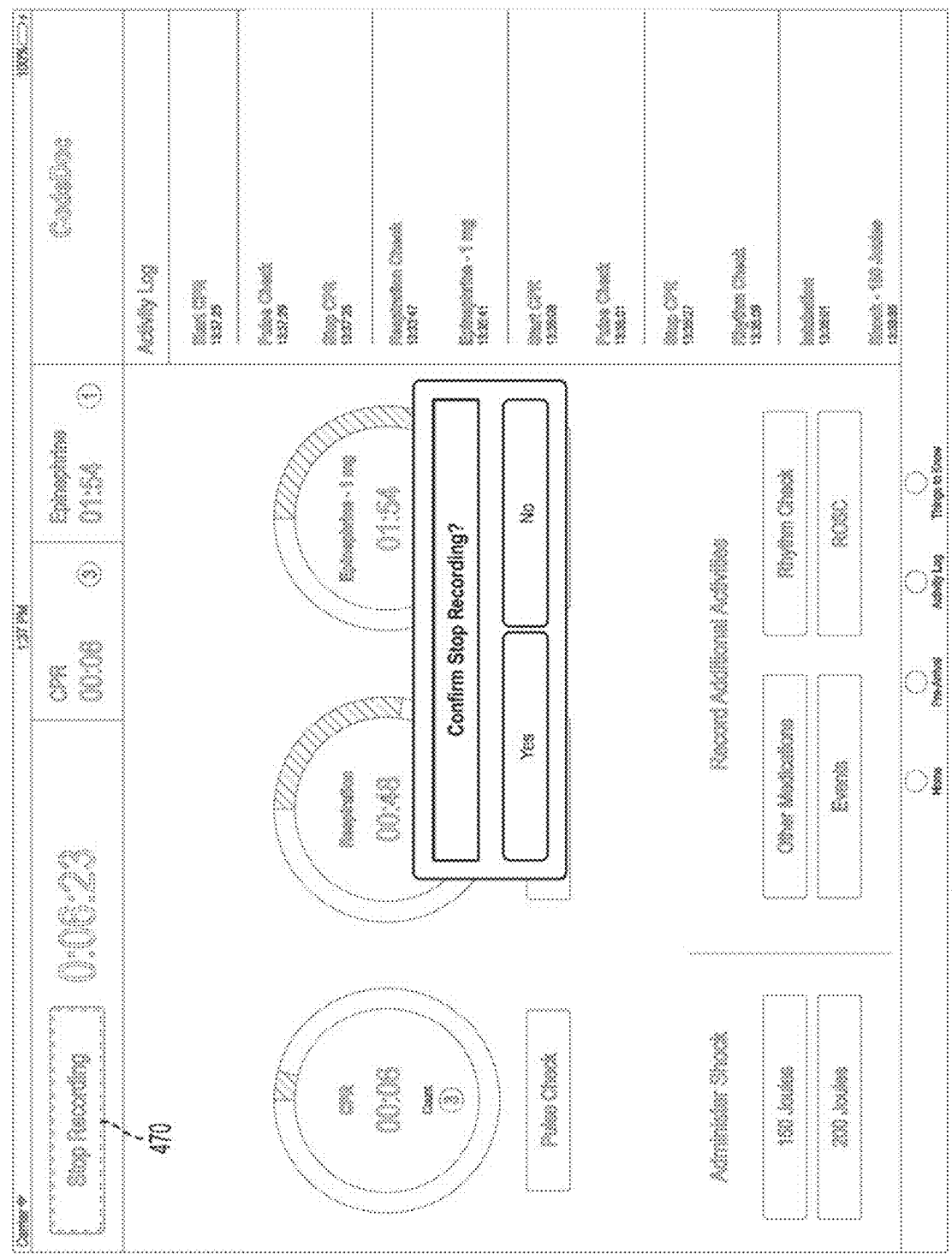
Figure 37:
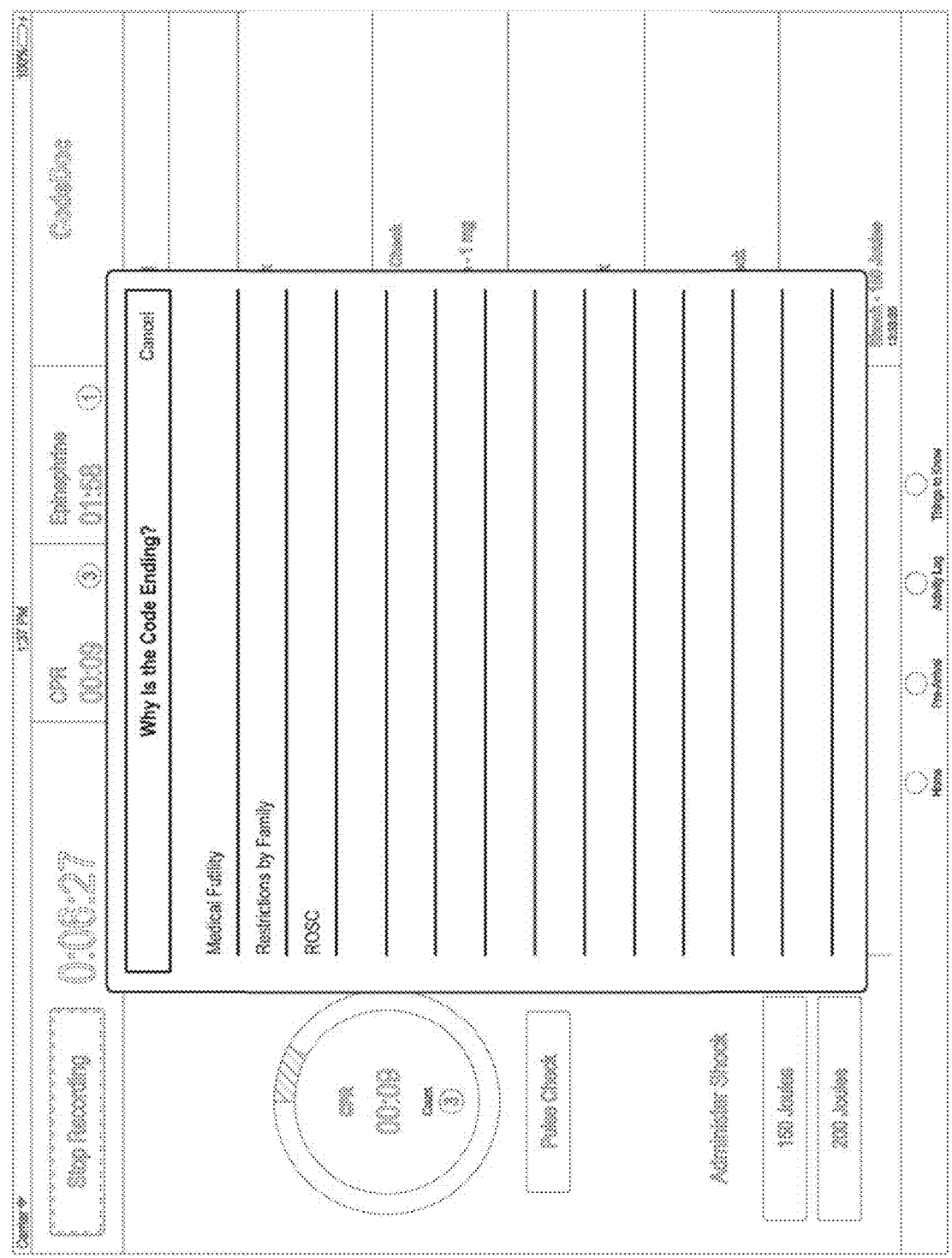
Figure 38:
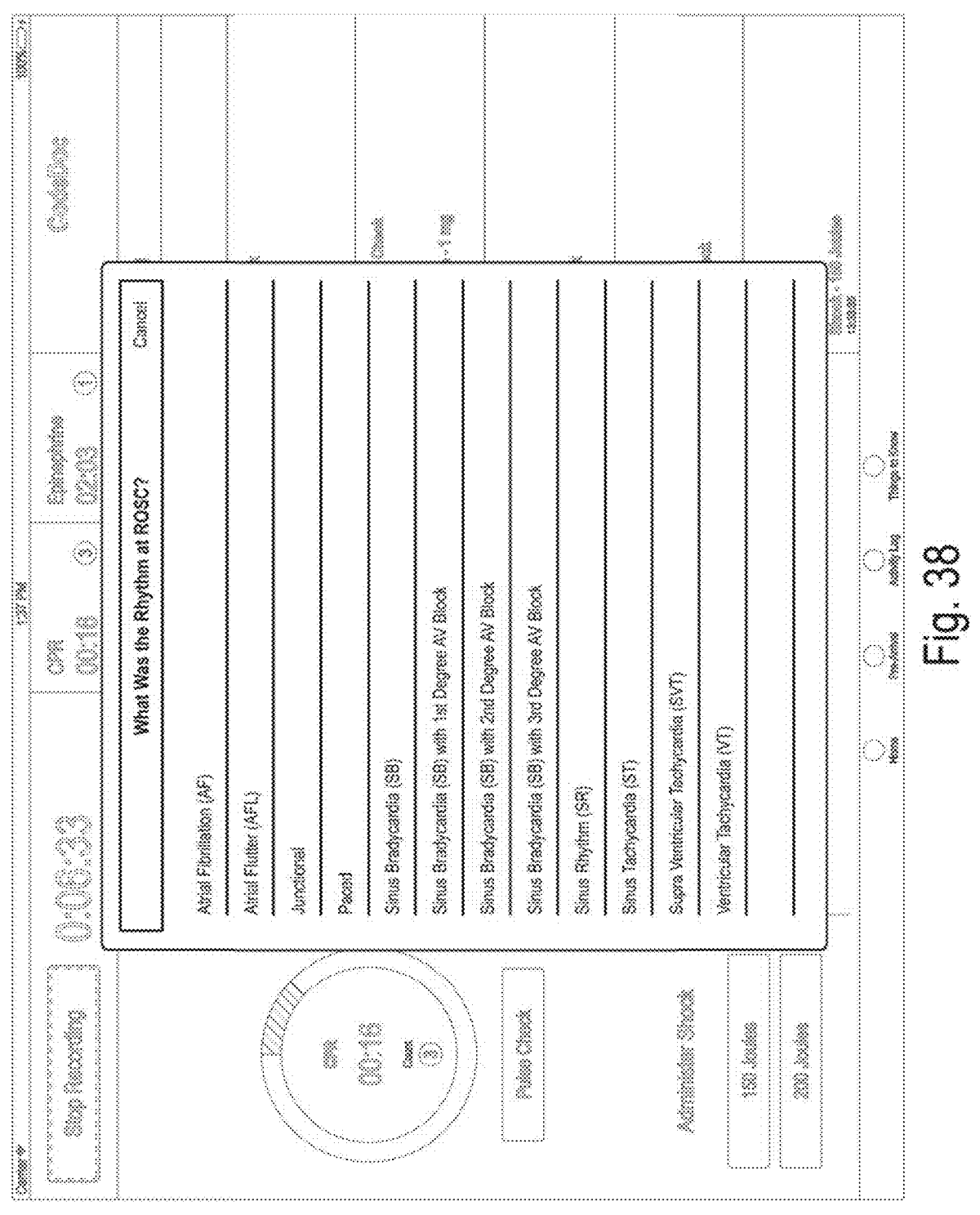
Figure 39:
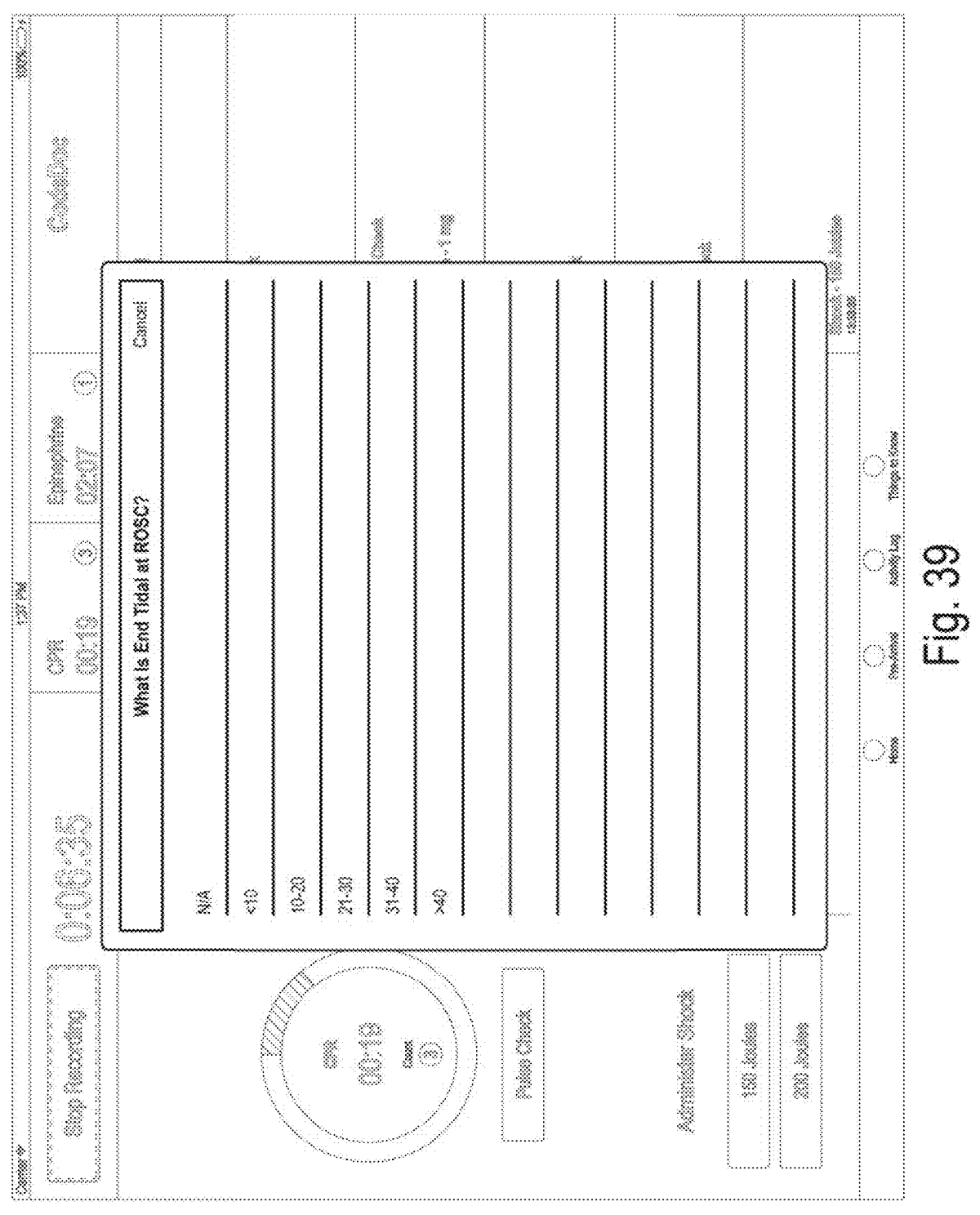
Figure 40:
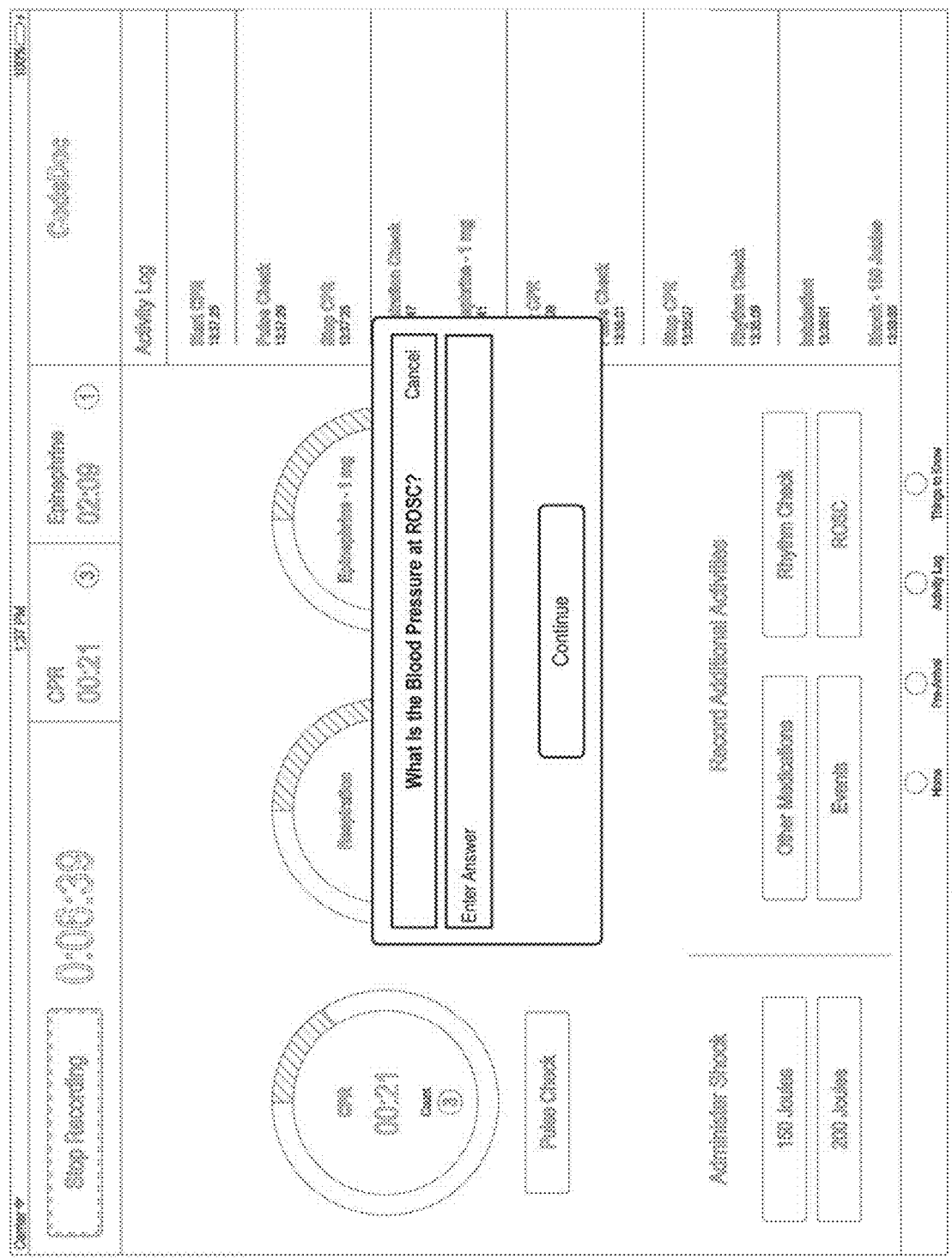
Figure 43:
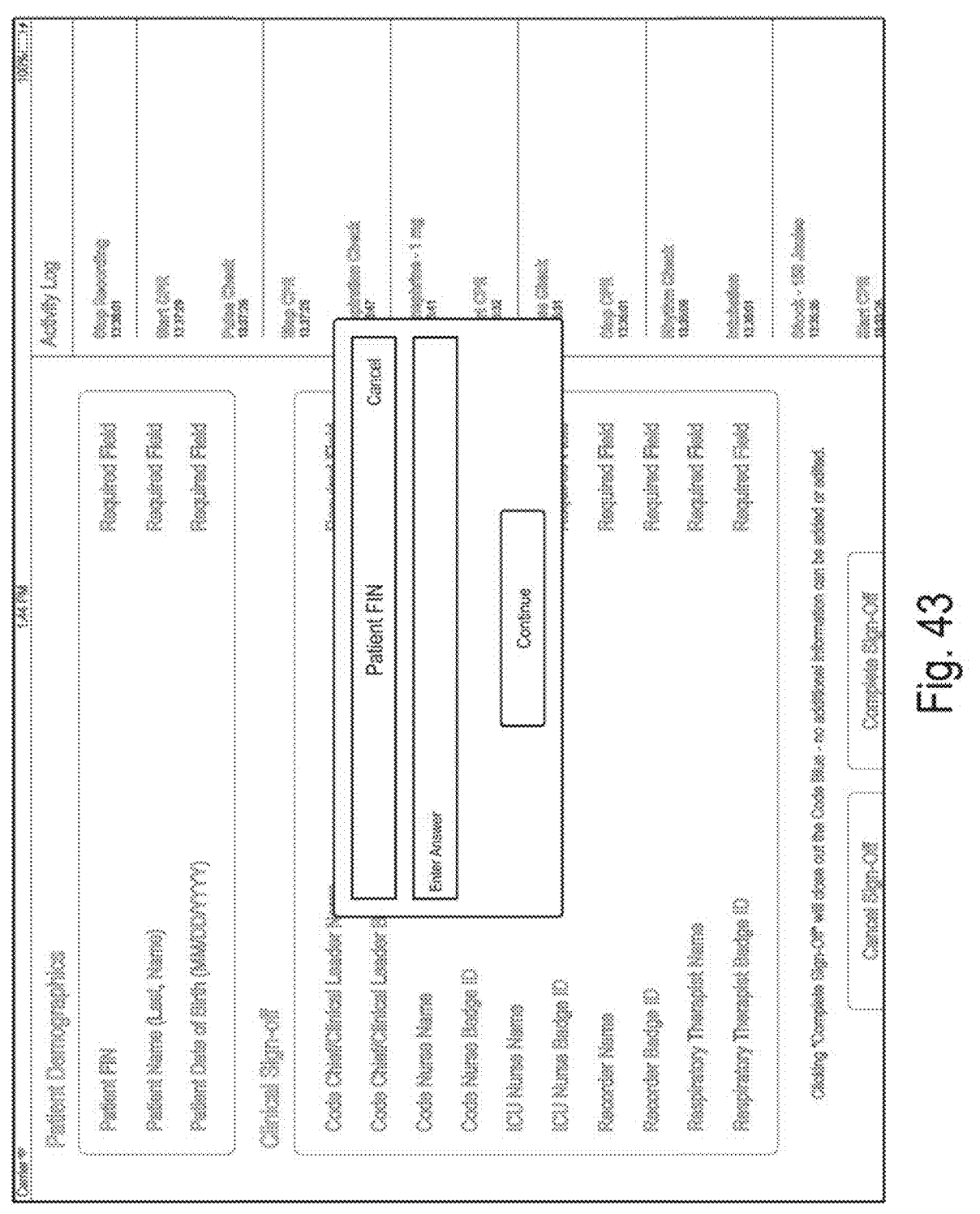
Figure 44:
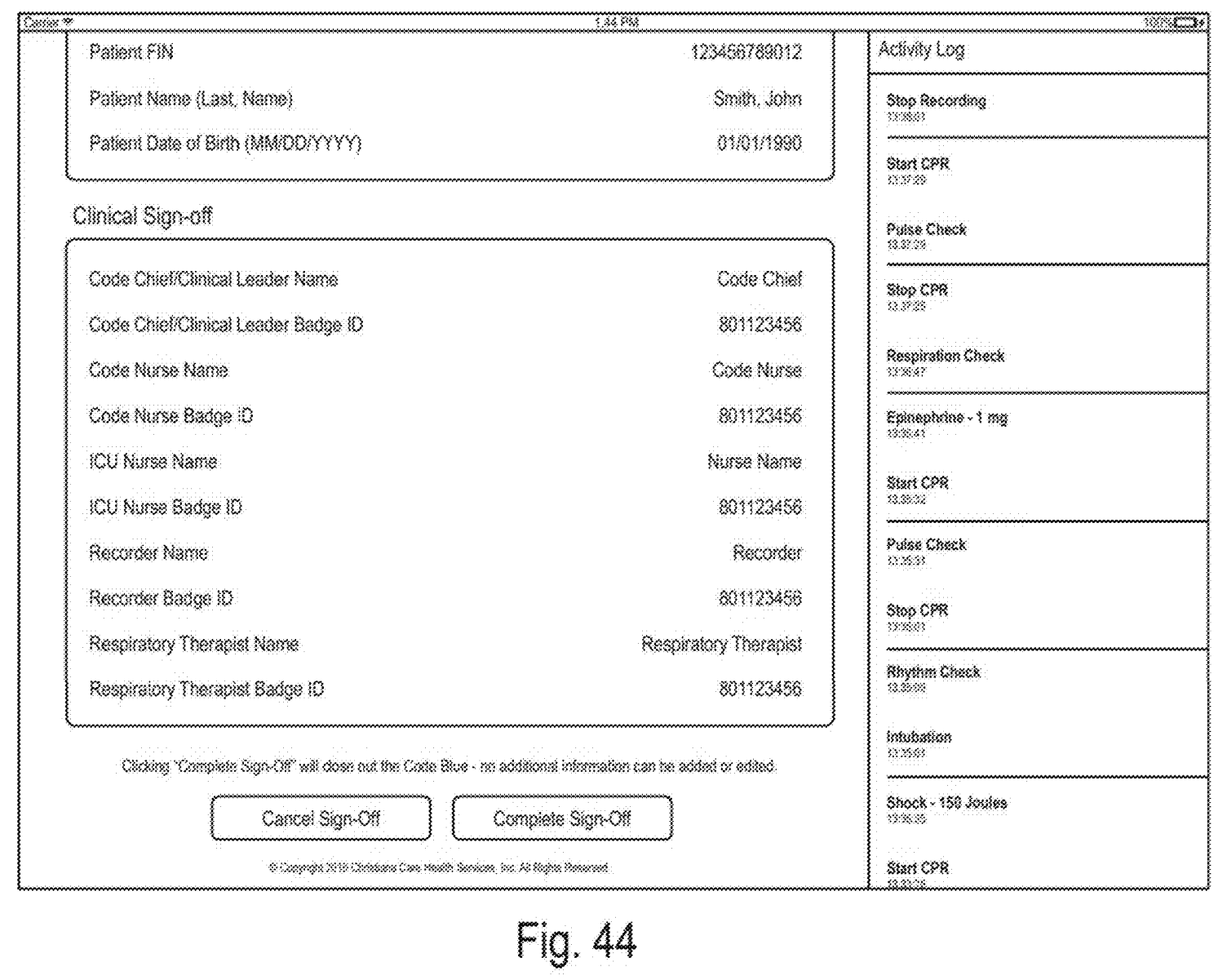

This continues until it is determined at 326 that the user has ended the session. This determination may be performed by the IE 150, and may be initiated by the operator of the CSS by selecting a STOP RECORDING button 470 displayed in the window 400, as shown in FIG. 36. The system may responsively display additional windows to guide the user to provide additional information to be recorded by the LE 190, as shown in FIGS. 37-45. Information may be gathered and recorded to comply with care protocol guidelines and/or care facility procedures/requirements. The LE 190 may gather all information, such as user input, time, count and other time-stamped event occurrences, into a report in electronic or other form and/or may gather such information into a data file in a common data format (such as an *.CSV, *.XLSX, *.MDB or other format) suitable for subsequent data processing using commercially-available data processing software, such as Microsoft Excel, Microsoft Access or other data analysis software such as Tableau or Microsoft Reporting Services.

In certain embodiments, the system may be configured to promote compliance with recordkeeping procedures. For example, the system may include instructions executable by the data processor to provide a logging engine configured to cause the display engine to display a login window requiring input of user credentials via the user input component prior to starting any timer. By way of example, the display engine may do so by displaying a login window requiring input of user credentials by optical scanning of machine-readable indicia, such as a two-dimensional bar code, on a physical identification card of a type generally used for personnel identification.

By way of the further example, the system may be configured to include instructions executable by the data processor to provide a logging engine configured to cause the display engine to display a logout window requiring completion of selected data input via the data input component prior to completion of a present care session and starting of a next session timer for a next care session. Accordingly, the system may effectively "force" a user to complete desired record keeping tasks in order to close out or complete a current session, and/or to prepare the device for use in a next session.

Optionally, the records may be stored in the memory and/or transmitted, e.g., over network 50, to an external system, such as server 200, for long-term storage, reporting, review, bulk record analysis, or other purposes.

Additionally, computer readable media storing computer readable code for carrying out the method steps identified above is provided. The computer readable media stores code for carrying out sub-processes for carrying out the methods described above.

A computer program product recorded on a computer readable medium for carrying out the method steps identified above is provided. The computer program product comprises computer readable means for carrying out the methods described above.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A computerized care support system comprising:
 a display device;
 a user input component;
 a memory operatively comprising a non-transitory data processor-readable medium;

a data processor operatively connected to the memory, the display, and the user input component; and user interface management instructions embodied in data processor-executable code stored in the memory, said user interface management instructions being executable by the data processor to provide a user interface display engine configured to:

display, via the display device, an entire management interface window within a physical display area of the display device;

display within the window, via the display device, a free-running session timer displaying an elapsed time of duration from a beginning of a session of use of the care support system to an end of the session of use of the care support system;

display within the window, via the display device, a plurality of independent cyclical task timers, each of said plurality of independent cyclical task timers having a different respective time interval cycle having a distinct cycle time duration corresponding to a distinct cyclical task;

in response to expiration of any one of said plurality of independent cyclical task timers:

display within the window, via the display device, at least one prompt corresponding to the expiration of said any one of said plurality of independent cyclical task timers, said prompt being specified by a predetermined care protocol.

2. The computerized care support system of claim 1, wherein said at least one prompt comprises a task-specific guided instruction sequence.

3. The computerized care support system of claim 2, wherein said task-specific guided instruction sequence comprise a plurality of related instructions, at least one of which is based upon branched logic, and is selectively displayed in response to prior user input provided in response to a prior displayed instruction.

4. The computerized care support system of claim 1, wherein said at least one prompt comprises a textual instruction to perform a medical care task.

5. The computerized care support system of claim 1, wherein said at least one prompt comprises a textual instruction to provide specific data input to the care support system via the user input component.

6. The computerized care support system of claim 1, said user interface management instructions further comprising instructions executable by the data processor to cause the user interface display engine to, in response to expiration of any one of said plurality of independent cyclical task timers:

augment a cycle counter corresponding to said one of said plurality of independent cyclical task timers;

store in said memory cycle count data;

display, via the display device, the augmented count in association with the associated task.

7. The computerized care support system of claim 6, said user interface management instructions further comprising instructions executable by the data processor to display within the window, via the display device, a plurality of visual progress indicators, each of said plurality of visual progress indicators corresponding to a respective one of said plurality of independent cyclical task timers and displaying in visual fashion a dynamic representation of a state of completion of said respective one of said plurality of independent cyclical task timers.

8. The computerized care support system of claim 7, wherein said user interface management instructions cause the user interface display engine to display each of said plurality of visual progress indicators as a progress bar in a shape defining an internal area, each cycle counter being displayed within a respective internal area of a respective one of said plurality of visual progress indicators.

9. The computerized care support system of claim 8, wherein said user interface management instructions cause the user interface display engine to display each of said plurality of independent cyclical task timers within a respective internal area of a respective one of said plurality of visual progress indicators.

10. The computerized care support system of claim 7, wherein said user interface management instructions cause the user interface display engine to display each of said plurality of visual progress indicators as a progress bar.

11. The computerized care support system of claim 7, wherein said user interface management instructions cause the user interface display engine to display each of said plurality of visual progress indicators as a progress bar in a shape defining an internal area, each of said plurality of independent cyclical task timers being displayed within a respective internal area of a respective one of said plurality of visual progress indicators.

12. The computerized care support system of claim 1, wherein said user interface management instructions further comprise instructions executable by the data processor to cause the user interface display engine to, in response to expiration of any one of said plurality of independent cyclical task timers:

reset and restart said one of said plurality of independent cyclical task timers.

13. The computerized care support system of claim 12, wherein said user interface management instructions cause the user interface display engine to display each of said plurality of independent cyclical task timers in a first color prior to expiration of the corresponding cycle interval, and in a second color different from said first color after expiration of the corresponding cycle interval.

14. The computerized care support system of claim 1, wherein each plurality of independent cyclical task timers is configured to count upwardly, and to continue running after expiration of a corresponding cycle interval.

15. The computerized care support system of claim 1, said user interface management instructions further comprising instructions executable by the data processor to provide a logging engine configured to:

store user input received via the user input component in the memory;

store time and count data in the memory;

create and store in memory a data file capturing the user input, time and count data, the data file being in a common data format suitable for subsequent data processing using commercially-available data processing software.

16. The computerized care support system of claim 15, wherein said user interface management instructions cause the user interface display engine to display within the window, via the display device, a scrolling event log identifying in continuous fashion time-stamped event occurrences logged by the logging engine at the computerized care support system.

17. The computerized care support system of claim 15, said user interface management instructions further comprising instructions executable by the data processor to provide a logging engine configured to:

cause the display engine to display a login window requiring input of user credentials via the user input component prior to starting any timer.

18. The computerized care support system of claim 17, said user interface management instructions further comprising instructions executable by the data processor to provide a logging engine configured to:
  cause the display engine to display a login window requiring input of user credentials by optical scanning of machine-readable indicia on a physical identification card.

19. The computerized care support system of claim 17, said user interface management instructions further comprising instructions executable by the data processor to provide a logging engine configured to:
  cause the display engine to display a logout window requiring completion of selected data input via the data input component prior to completion of a present care session and starting of a next session timer for a next care session.

20. A computerized care support system comprising:
  a display device;
  a user input component;
  a memory operatively comprising a non-transitory data processor-readable medium;
  a data processor operative connected to the memory, the display and the user input component; and
  user interface management instructions embodied in data processor-executable code stored in the memory, said user interface management instructions being executable by the data processor to provide a user interface display engine configured to:
    display, via the display device, an entire management interface window within a physical display area of the display device;
    display within the window, via the display device, a free-running session timer displaying an elapsed time of duration from a beginning of a session of use of the care support system to an end of the session of use of the care support system;
    display within the window, via the display device, a plurality of independent cyclical task timers distinct from said free-running session timer, each of said plurality of independent cyclical task timers having a different respective prescribed time interval cycle having a distinct cycle time duration corresponding to a distinct cyclical task; and
    display within the window, via the display device, a plurality of visual progress indicators, each of said plurality of visual progress indicators corresponding to a respective one of said plurality of independent cyclical task timers and displaying in visual fashion a dynamic representation of a state of completion of said respective one of said plurality of independent cyclical task timers.

21. The computerized care support system of claim 20, said user interface management instructions further comprising instructions executable by the data processor to cause the user interface display engine to, in response to expiration of any one of said plurality of independent cyclical task timers:
  display within the window, via the display device, at least one prompt corresponding to the expiration of said any one of said plurality of independent cyclical task times, said prompt being specified a predetermined care protocol.

22. The computerized care support system of claim 21, wherein said at least one prompt comprises a task-specific guided instruction sequence.

23. The computerized care support system of claim 21, wherein said task-specific guided instruction sequence comprise a plurality of related instructions, at least one of which is based upon branched logic, and is selectively displayed in response to prior user input provided in response to a prior displayed instruction.

24. The computerized care support system of claim 21, wherein said at least one prompt comprises a textual instruction to perform a medical care task.

25. The computerized care support system of claim 21, wherein said at least one prompt comprises a textual instruction to provide specific data input to the care support system via the user input component.

26. The computerized care support system of claim 20, said user interface management instructions further comprising instructions executable by the data processor to cause the user interface display engine to, in response to expiration of any one of said plurality of independent cyclical task timers:
  augment a cycle counter corresponding to said one of said plurality of independent cyclical task timers;
  store in said memory cycle count data; and
  display, via the display device, the augmented count in association with the associated task.

27. The computerized care support system of claim 26, said user interface management instructions further comprising instructions executable by the data processor to display within the window, via the display device, a plurality of visual progress indicators, each of said plurality of visual progress indicators corresponding to a respective one of said plurality of independent cyclical task timers and displaying in visual fashion a dynamic representation of a state of completion of said respective one of said plurality of independent cyclical task timers.

28. The computerized care support system of claim 27, wherein said user interface management instructions cause the user interface display engine to display each of said plurality of visual progress indicators as a progress bar in a shape defining an internal area, each cycle counter being displayed within a respective internal area of a respective one of said plurality of visual progress indicators.

29. The computerized care support system of claim 28, wherein said user interface management instructions cause the user interface display engine to display each of said plurality of independent cyclical task timers within a respective internal area of a respective one of said plurality of visual progress indicators.

30. The computerized care support system of claim 27, wherein said user interface management instructions cause the user interface display engine to display each of said plurality of visual progress indicators as a progress bar in a shape defining an internal area, each of said plurality of independent cyclical task timers being displayed within a respective internal area of a respective one of said plurality of visual progress indicators.

31. The computerized care support system of claim 20, wherein each plurality of independent cyclical task timers is configured to count upwardly, and to continue running after expiration of a corresponding cycle interval.

32. The computerized care support system of claim 31, wherein said user interface management instructions cause the user interface display engine to display each of said plurality of independent cyclical task timers in a first color prior to expiration of the corresponding cycle interval, and in a second color different from said first color after expiration of the corresponding cycle interval.

33. The computerized care support system of claim 20, said user interface management instructions further comprising instructions executable by the data processor to provide a logging engine configured to:
store user input received via the user input component in the memory;
store time and count data in the memory;
create and store in memory a data file capturing the user input, time and count data, the data file being in a common data format suitable for subsequent data processing using commercially-available data processing software.

34. The computerized care support system of claim 33, wherein said user interface management instructions cause the user interface display engine to display within the window, via the display device, a scrolling event log identifying in continuous fashion time-stamped event occurrences logged by the logging engine at the computerized care support system.

35. The computerized care support system of claim 33, said user interface management instructions further comprising instructions executable by the data processor to provide a logging engine configured to:
cause the display engine to display a login window requiring input of user credentials via the user input component prior to starting any timer.

36. The computerized care support system of claim 35, said user interface management instructions further comprising instructions executable by the data processor to provide a logging engine configured to:
cause the display engine to display a login window requiring input of user credentials by optical scanning of machine-readable indicia on a physical identification card.

37. The computerized care support system of claim 35, said user interface management instructions further comprising instructions executable by the data processor to provide a logging engine configured to:
cause the display engine to display a logout window requiring completion of selected data input via the data input component prior to completion of a present care session and starting of a next session timer for a next care session.

38. A method of controlling a display of a computerized device comprising a display device, a user input component, a memory operatively comprising a non-transitory data processor-readable medium, a data processor operatively connected to the memory, the display, and the user input component, and user interface management instructions embodied in data processor-executable code stored in the memory and executable by the data processor, the method comprising:
displaying, via the display device, an entire management interface window within a physical display area of the display device;
displaying within the window, via the display device, a free-running session timer displaying an elapsed time of duration from a beginning of a session of use of the care support system to an end of the session of use of the care support system;
displaying within the window, via the display device, a plurality of independent cyclical task timers, each of said plurality of independent cyclical task timers having a different respective time interval cycle having a distinct cycle time duration corresponding to a distinct cyclical task; and
in response to expiration of any one of said plurality of independent cyclical task timers:
displaying within the window, via the display device, at least one prompt corresponding to the expiration of said any one of said plurality of independent cyclical task timers, said prompt being specified by a predetermined care protocol.

39. The method of claim 38, further comprising, in response to expiration of any one of said plurality of independent cyclical task timers:
augmenting a cycle counter corresponding to said one of said plurality of independent cyclical task timers;
storing in said memory cycle count data; and
displaying, via the display device, the augmented count in association with the associated task.

40. The method of claim 38, further comprising:
displaying within the window, via the display device, a plurality of visual progress indicators, each of said plurality of visual progress indicators corresponding to a respective one of said plurality of independent cyclical task timers and displaying in visual fashion a dynamic representation of a state of completion of said respective one of said plurality of independent cyclical task timers.

41. The method of claim 40, further comprising:
displaying each of said plurality of visual progress indicators as a progress bar in a shape defining an internal area, each cycle counter being displayed within a respective internal area of a respective one of said plurality of visual progress indicators.

42. The method of claim 41, further comprising:
displaying each of said plurality of independent cyclical task timers within a respective internal area of a respective one of said plurality of visual progress indicators.

43. The method of claim 38, further comprising:
displaying each of said plurality of independent cyclical task timers in a first color prior to expiration of a corresponding cycle interval, and in a second color different from said first color after expiration of the corresponding cycle interval.

44. The method of claim 38, further comprising:
storing user input received via the user input component in the memory;
storing time and count data in the memory;
creating and storing in memory a data file capturing the user input, time and count data, the data file being in a common data format suitable for subsequent data processing using commercially-available data processing software.

45. The method of claim 38, further comprising:
displaying within the window, via the display device, a scrolling event log identifying in continuous fashion time-stamped event occurrences logged by the logging engine at the computerized care support system.

46. The method of claim 38, further comprising:
displaying a login window requiring input of user credentials via the user input component prior to starting any timer.

47. The method of claim 38, further comprising:
displaying a login window requiring input of user credentials by optical scanning of machine-readable indicia on a physical identification card.

48. The method of claim 38, further comprising:
displaying a logout window requiring completion of selected data input via the data input component prior to completion of a present care session and starting of a next session timer for a next care session.

49. A computer program product for implementing a method of controlling a display of a computerized device, the computer program product comprising a non-transitory computer-readable medium storing executable instructions that, when executed by a processor, cause a computerized care support system to perform a method comprising:
- displaying, via the display device, an entire management interface window within a physical display area of the display device;
- displaying within the window, via the display device, a free-running session timer displaying an elapsed time of duration from a beginning of a session of use of the care support system to an end of the session of use of the care support system;
- displaying within the window, via the display device, a plurality of independent cyclical task timers, each of said plurality of independent cyclical task timers having a different respective time interval cycle having a distinct cycle time duration corresponding to a distinct cyclical task; and
- in response to expiration of any one of said plurality of independent cyclical task timers:
  - displaying within the window, via the display device, at least one prompt corresponding to the expiration of said any one of said plurality of independent cyclical task timers, said prompt being specified by a predetermined care protocol.

50. A computer program product for implementing a method of controlling a display of a computerized device, the computer program product comprising a non-transitory computer-readable medium storing executable instructions that, when executed by a processor, cause a computerized care support system to perform a method comprising:
- displaying, via the display device, an entire management interface window within a physical display area of the display device;
- displaying within the window, via the display device, a free-running session timer displaying an elapsed time of duration from a beginning of a session of use of the care support system to an end of the session of use of the care support system;
- displaying within the window, via the display device, a plurality of independent cyclical task timers, each of said plurality of independent cyclical task timers having a different respective time interval cycle having a distinct cycle time duration corresponding to a distinct cyclical task; and
- displaying within the window, via the display device, a plurality of visual progress indicators, each of said plurality of visual progress indicators corresponding to a respective one of said plurality of independent cyclical task timers and displaying in visual fashion a dynamic representation of a state of completion of said respective one of said plurality of independent cyclical task timers.

* * * * *